(12) United States Patent
Poustka et al.

(10) Patent No.: US 9,752,985 B2
(45) Date of Patent: Sep. 5, 2017

(54) METHOD AND DEVICES FOR APPLYING SUBSTANCES TO A SUPPORT, ESPECIALLY MONOMERS FOR THE COMBINATORIAL SYNTHESIS OF MOLECULE LIBRARIES

(75) Inventors: Annemarie Poustka, Heidelberg (DE); Frank Breitling, Heidelberg (DE); Karl-Heinz Gross, Dossenheim (DE); Stefan Dübel, Dossenheim (DE); Rainer Saffrich, Dossenheim (DE)

(73) Assignees: DEUTSCHES KREBSFORSCHUNGSZENTRUM STIFTUNG DES ÖFFENTLICHEN RECHTS, Heidelberg (DE); EUROPÄISCHES LABORATORIUM FÜR MOLEKULARBIOLOGIE, Heidelberg (DE)

( * ) Notice: Subject to any disclaimer, the term of this patent is extended or adjusted under 35 U.S.C. 154(b) by 1277 days.

(21) Appl. No.: 09/880,688

(22) Filed: Jun. 13, 2001

(65) Prior Publication Data

US 2002/0006672 A1 Jan. 17, 2002

Related U.S. Application Data

(63) Continuation of application No. PCT/DE99/03982, filed on Dec. 14, 1999.

(30) Foreign Application Priority Data

Dec. 14, 1998 (DE) .................. 198 57 529
Jul. 30, 1999 (DE) .................. 199 35 553

(51) Int. Cl.
| | | |
|---|---|---|
| G01N 21/64 | (2006.01) |
| B01J 19/00 | (2006.01) |
| B82Y 30/00 | (2011.01) |
| C07K 1/04 | (2006.01) |
| C40B 40/10 | (2006.01) |
| C40B 60/14 | (2006.01) |
| C40B 70/00 | (2006.01) |

(52) U.S. Cl.
CPC ...... *G01N 21/6452* (2013.01); *B01J 19/0046* (2013.01); *B82Y 30/00* (2013.01); *C07K 1/047* (2013.01); *G01N 21/6428* (2013.01); *B01J 2219/0059* (2013.01); *B01J 2219/0061* (2013.01); *B01J 2219/00378* (2013.01); *B01J 2219/00441* (2013.01); *B01J 2219/00542* (2013.01); *B01J 2219/00585* (2013.01); *B01J 2219/00596* (2013.01); *B01J 2219/00605* (2013.01); *B01J 2219/00626* (2013.01); *B01J 2219/00641* (2013.01); *B01J 2219/00659* (2013.01); *B01J 2219/00711* (2013.01); *B01J 2219/00725* (2013.01); *C40B 40/10* (2013.01); *C40B 60/14* (2013.01); *C40B 70/00* (2013.01)

(58) Field of Classification Search
None
See application file for complete search history.

(56) References Cited

U.S. PATENT DOCUMENTS

| | | | | |
|---|---|---|---|---|
| 4,912,032 A * | 3/1990 | Hoffman et al. | ............ | 435/7.1 |
| 5,185,226 A * | 2/1993 | Grosso et al. | ............ | 430/45.33 |
| 5,318,679 A * | 6/1994 | Nishioka | ................ | 204/157.68 |
| 5,445,934 A * | 8/1995 | Fodor et al. | ................... | 506/16 |
| 5,449,754 A * | 9/1995 | Nishioka | ..................... | 530/334 |
| 5,510,270 A * | 4/1996 | Fodor et al. | ................ | 436/518 |
| 5,581,337 A * | 12/1996 | Suzuki | ........................ | 399/263 |
| 5,750,318 A * | 5/1998 | Lambert et al. | ............ | 430/346 |
| 6,028,189 A * | 2/2000 | Blanchard | ..................... | 506/27 |
| 6,951,682 B1 * | 10/2005 | Zebala | ....................... | 428/312.2 |
| 7,179,638 B2 * | 2/2007 | Anderson et al. | ......... | 435/287.2 |
| 2004/0062911 A1 * | 4/2004 | Lauf et al. | .................... | 428/138 |

FOREIGN PATENT DOCUMENTS

| | | | | |
|---|---|---|---|---|
| WO | WO 97/44134 A | | 11/1997 | |
| WO | WO 98/12559 | * | 3/1998 | ............ G01N 33/53 |
| WO | WO 98/12559 A | | 3/1998 | |
| WO | WO9822250 | * | 5/1998 | |
| WO | WO9851408 | * | 5/1998 | |
| WO | WO9851408 | * | 11/1998 | |
| WO | WO 99/52625 A | | 10/1999 | |
| WO | WO 00/15653 A | | 3/2000 | |

OTHER PUBLICATIONS

Fodor, S. P. A.; Read, L.; Pirrung, M. C.; Stryer, L.; Lu, A. T. Solas, D. "Light-Directed, Spatially Addressable Parallel Chemical Synthesis" Science 1991, 251, 767-773.*

Yan, B.; Gremlich, H. -U. "Role of Fourier Transform infrared spectroscopy in the rehearsal phase of combinatorial chemistry: a thin-layer chromatography equivalent for on-support monitoring of solid-phase organic synthesis" J. Chromatogr. B: Biomed. Sci. Applic. 1999, 725, 91-102.*

(Continued)

*Primary Examiner* — Juliet Switzer
*Assistant Examiner* — Sahana Kaup
(74) *Attorney, Agent, or Firm* — Law Firm of Ursula B. Day

(57) ABSTRACT

For the combinatorial synthesis of molecule libraries, substances are embedded in a matrix consisting of a first solvent thereby forming transport units in a solid state of aggregation at a temperature of less than 90° C. and wherein after application to a support, the physical environment of the transport units is modified by the application of a physical process such as a laser printer whereby the substances in the transport units are linked to the support.

16 Claims, 20 Drawing Sheets

(56) References Cited

OTHER PUBLICATIONS

Figure 1:
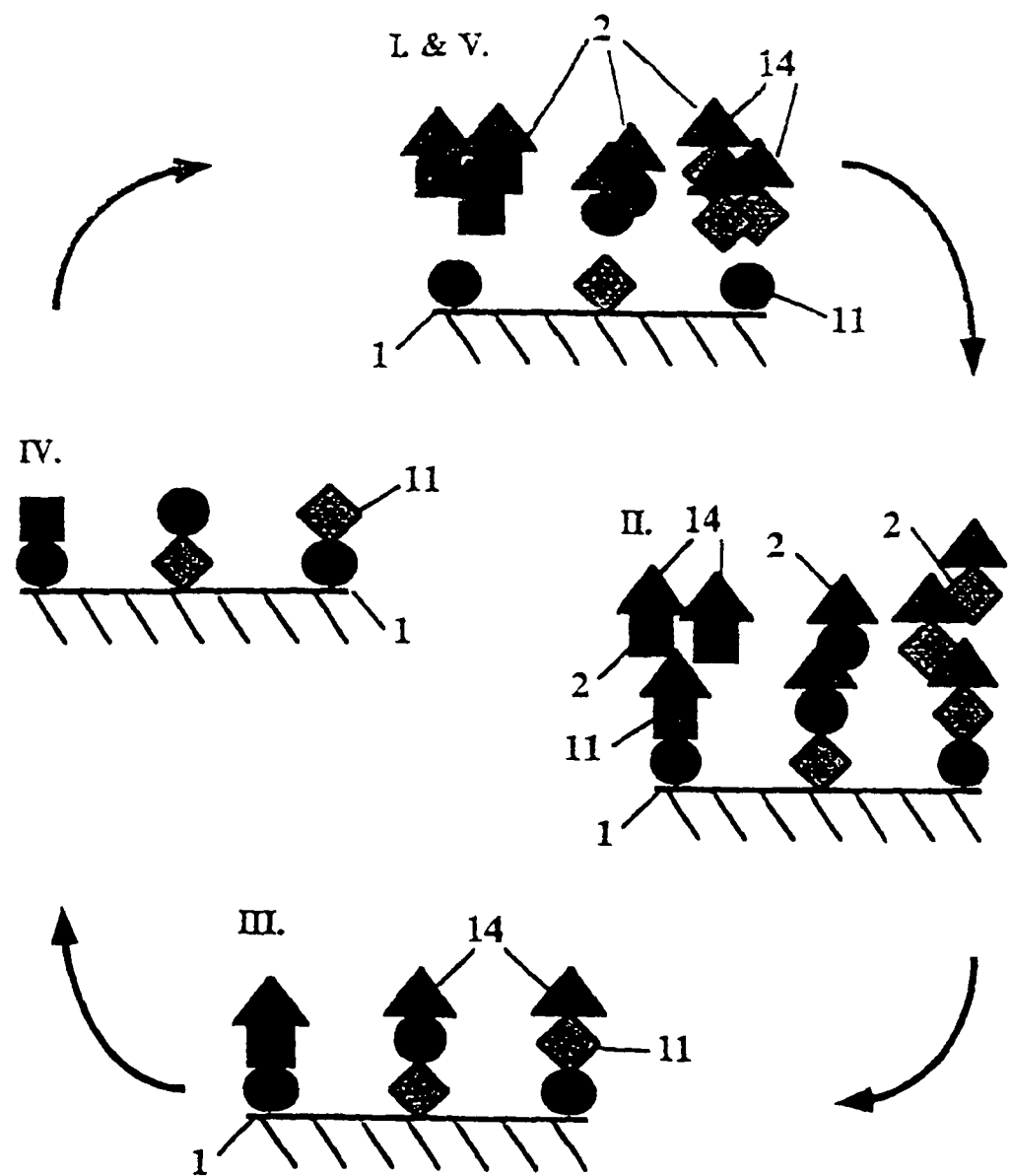

Calvert, P. "Inkjet Printing for Materials and Devices" Chem. Mater. 2001, 13, 3299-3305.*
The Condensed Chemical Dictionary, $9^{th}$ ed. ,Hawley 1980, p. 726.*

* cited by examiner

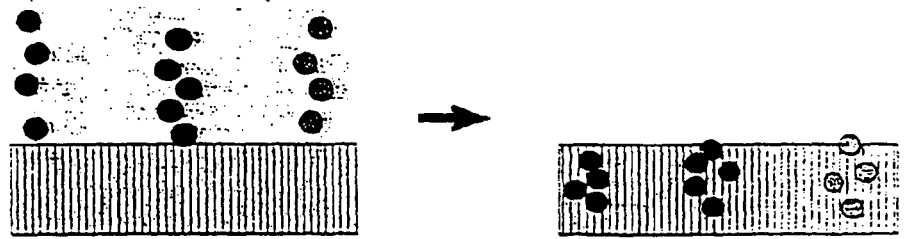
Demand on spotting of color
- Low diffusion rate of the large chromphors
- Rapidly evaporating solvent
- Absorbent paper
Demand on spotting of monomers for the combinatorial synthesis
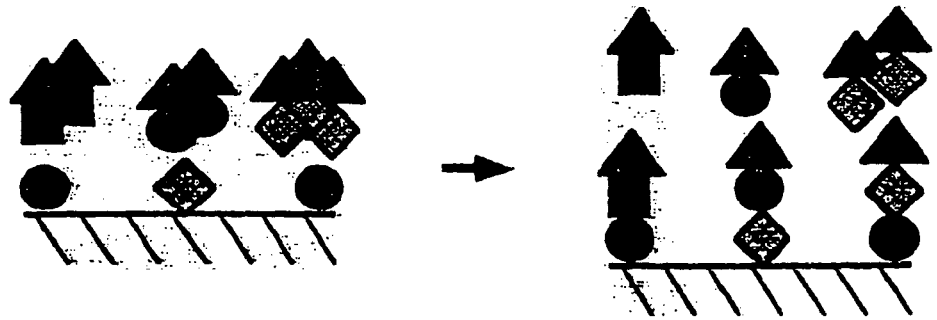
- High diffusion rate of small monomers
- Very slowly evaporating solvent
Fig. 6

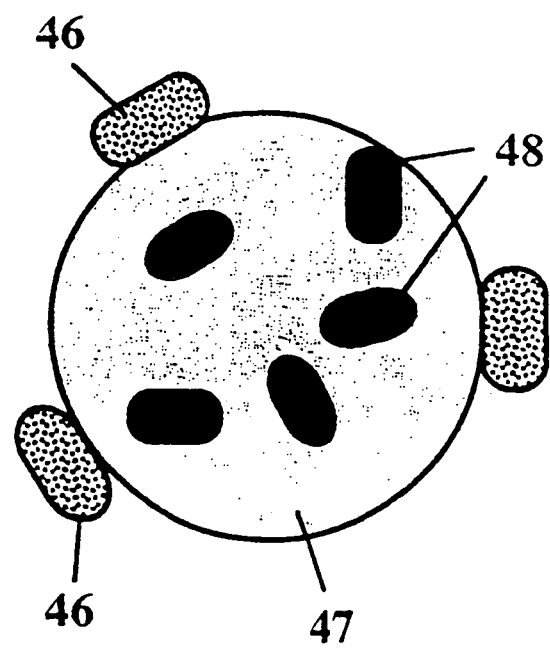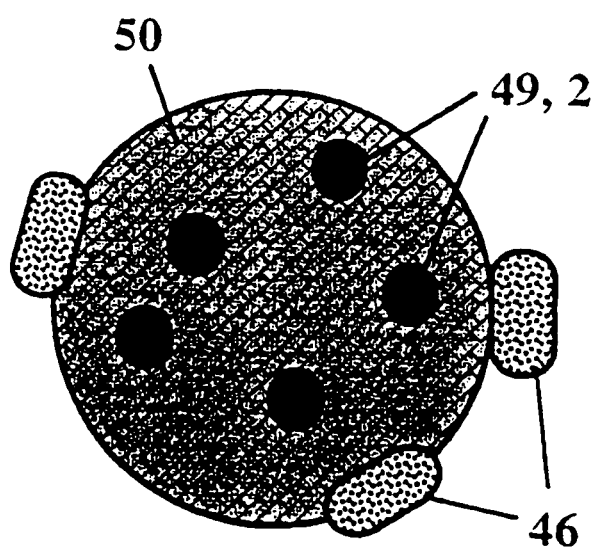
Fig. 7 ca 20cm ca 30cm

DinA4 Page 600 dpi = 600 dots per inch
600 dpi = ca 1 dot all 40μm
1.200 dpi = ca 1 dot all 20μm
2.400 dpi = ca 1 dot all 10μm
4.800 dpi = ca 1 dot all 5μm Dots per DinA4 Page:
600 dpi = ca 5.000 x 7.500 = ca 30 millions dots
1.200 dpi = ca 10.000 x 15.000 = ca 125 millions dots
2.400 dpi = ca 20.000 x 30.000 = ca 500 millions dots
4.800 dpi = ca 40.000 x 60.000 = ca 2 milliards dots

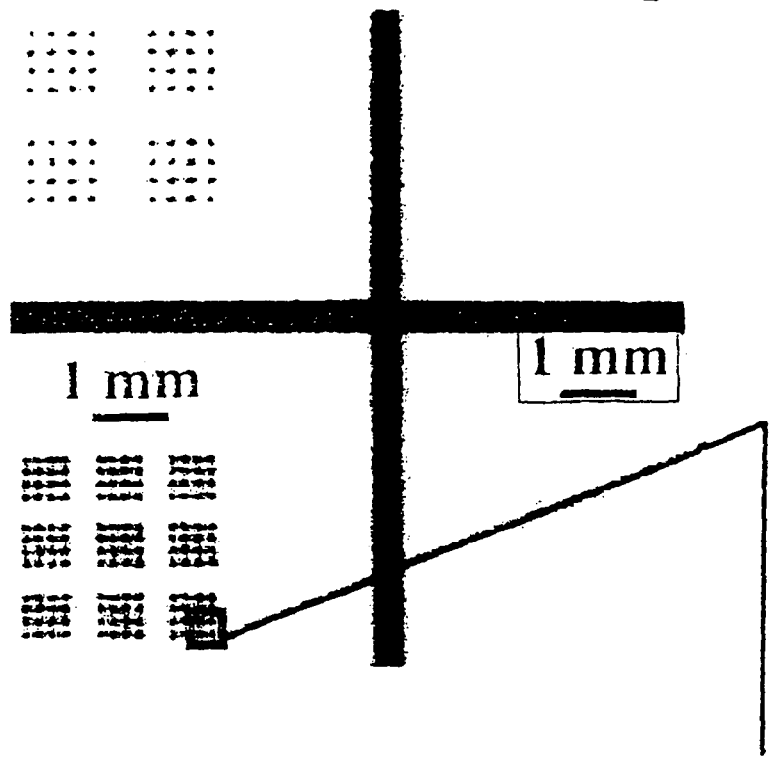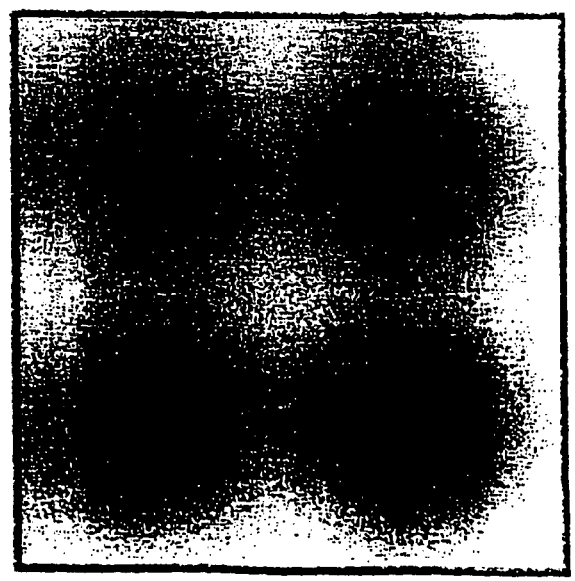
Fig. 11

Heptamers $20^1 = 20$ different amino acids $20^2 = 400$ different dipeptides $20^3 = 8.000$ different tripeptides $20^4 = 160.000$ different tetrapeptides $20^5 = 3,2$ millions different pentapeptides $20^6 = 64$ millions different hexapeptides $20^7 = 1.280$ millions different heptapeptides

complete tripeptide library:
= $20^3$ = 8.000 different peptide
complete tetrapeptide library:
= $20^4$ = 160.000 different peptide
complete pentapeptide library:
= $20^5$ = 3,2 millions different peptide
complete hexapeptide library:
= $20^6$ = 64 millions different peptide
Z = set amino acid position
X = Mixture of 20 different amino acid
Fig. 15

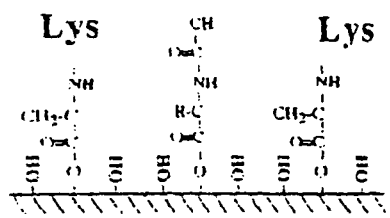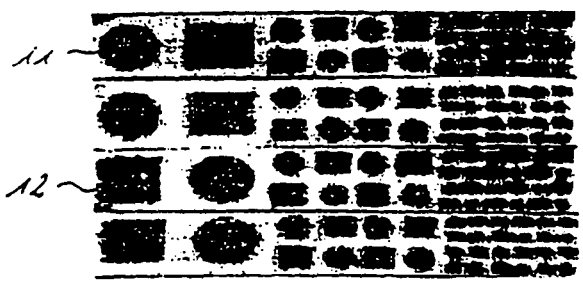
Fig. 20

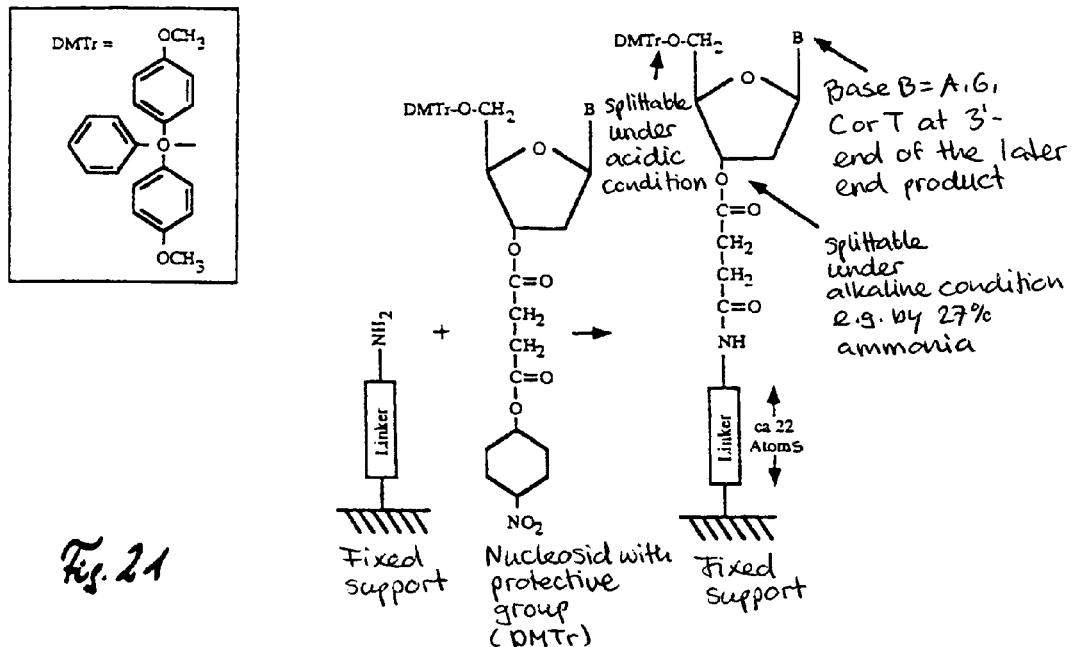
Fig. 21
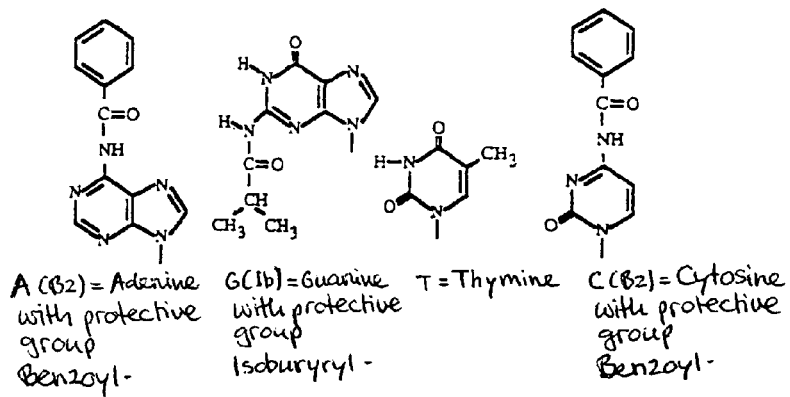
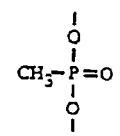 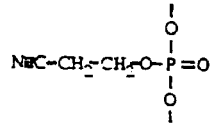
Fig. 22

METHOD AND DEVICES FOR APPLYING SUBSTANCES TO A SUPPORT, ESPECIALLY MONOMERS FOR THE COMBINATORIAL SYNTHESIS OF MOLECULE LIBRARIES

CROSS-REFERENCES TO RELATED APPLICATIONS

This application is a continuation of prior filed copending PCT International application no. PCT/DE99103982, filed Dec. 14, 1999.

This application claims the priorities of German Patent Application Serial No. 198 57 529.7, filed Dec. 14, 1998, and German Patent Application Serial No. 199 35 553.3, filed Jul. 30, 1999, the subject matter of which is incorporated herein by reference.

BACKGROUND OF THE INVENTION

The invention relates to methods and devices for applying substances to a support, especially monomers for the combinatorial synthesis of molecule libraries as used in the detection of optical properties, more especially of luminescence reactions and refraction behaviour, of molecules bound on the support.

In the following description, the term "molecule library" denotes the entirety of many different molecules bound at defined places on a support, whereby the various molecules are arranged as compactly as possible. The molecule libraries to which the invention relates are formed hereby more especially by the combinatorial synthesis of a limited number of monomers. The principle of combinatorial synthesis is explained schematically in FIG. 1.

The term "highly complex" denotes molecule libraries having more than $10^3$ different representatives, more especially however molecule libraries having more than $10^5$ different representatives.

Said complex molecule libraries can be applied particularly advantageously to a two-dimensional support whereby each different member of the molecule library can then be allocated a locally precisely defined place on the support. This means that a locally precisely defined reaction e.g. a staining reaction permits exact and unique conclusions to be reached on the support-bound reaction partner. The locally precisely defined places with the defined member of said molecule library are also called spots and the entirety of the molecule libraries on the two-dimensional support are also called arrays.

The two-dimensional array can have a smooth surface and be essentially impenetrable for the solvents used. However, it can also exhibit a porous structure compared thereto so that a third dimension is revealed to the solvents used and the substances to be linked. Supports of this type are particularly indispensable if the signal strength is to be increased compared with a support having a smooth surface. This is particularly the case when, for example, an array of peptides is to be stained with the blood serum of a patient and the binding signals of relatively weakly concentrated antibody reactivities are also to be detected.

Subsequently the synonymous terms "two-dimensional support" or "array" thus mean both supports where different molecules are essentially arranged in only two dimensions and also porous supports where the various molecules are present in an additional third dimension, thus are no longer (essentially two-dimensional) arrays in the real sense.

The term "solid state of aggregation" also includes undercooled liquids.

The term "properties" is understood in the broadest sense and should include not only the properties characteristic of specific molecules, such as for example their mass spectrogram but, for example, also the capability in general, namely by the mere presence, of displaying a certain reaction so that the invention thus also relates to such methods and devices for which initially only the mere presence of a substance, but not its type, should be concluded from a particular optical reaction (whereby the type of substance is then determined for example from its position on the support).

The term "biological" molecules is here taken to mean all types of molecules particularly relevant in biology, pharmacy and medicine, thus for example, peptides, D-peptides, L-peptides and mixtures thereof, naturally occurring oligonucleotides, their mirror images and mixtures thereof, artificially derivatised oligonucleotides, such as those used for construction of aptamers, oligosaccharides and modifications of said molecules. More especially, modular constructed oligomers which do not occur in nature can have particular pharmacological relevance. Particular mention in this connection may be made of non-natural substances produced with the aid of chemical combinatorial analysis which can be used as ligands of biological molecules, more especially organic compounds, steroid derivatives and so on. From many of these molecules specific binders can be isolated for a naturally occurring molecule which modify the activity of this molecule. However, since these binders frequently cannot be detached from naturally occurring digestive enzymes, they are especially suitable for use as therapeutics.

Various methods and devices are known for the synthesis of highly complex molecule libraries but these possess certain disadvantages. Thus the known methods require costly and expensive special equipment for their implementation and are comparatively slow in the readout of a luminescence signal. In particular, if, as is advantageous for different reasons as will be explained subsequently, very many different molecular groups are to be arranged on a common support and investigated singly, very expensive mechanics must be used to activate the individual molecular groups, which is not only expensive and liable to breakdown but also always exhibits manufacturing tolerances in maximum precision work, which are several orders of magnitude higher than the minimum size of the molecular groups sufficient for an investigation. As a result, the maximum number of molecules or molecular groups to be accommodated on a support is limited for known methods and devices and is roughly in the order of magnitude of a few $10^5$ molecular groups. In particular for certain blood serum or DNA analyses, however, it would be desirable if approximately $10^8$ to $10^9$ molecules could be accommodated and studied on one support.

Figure 2:
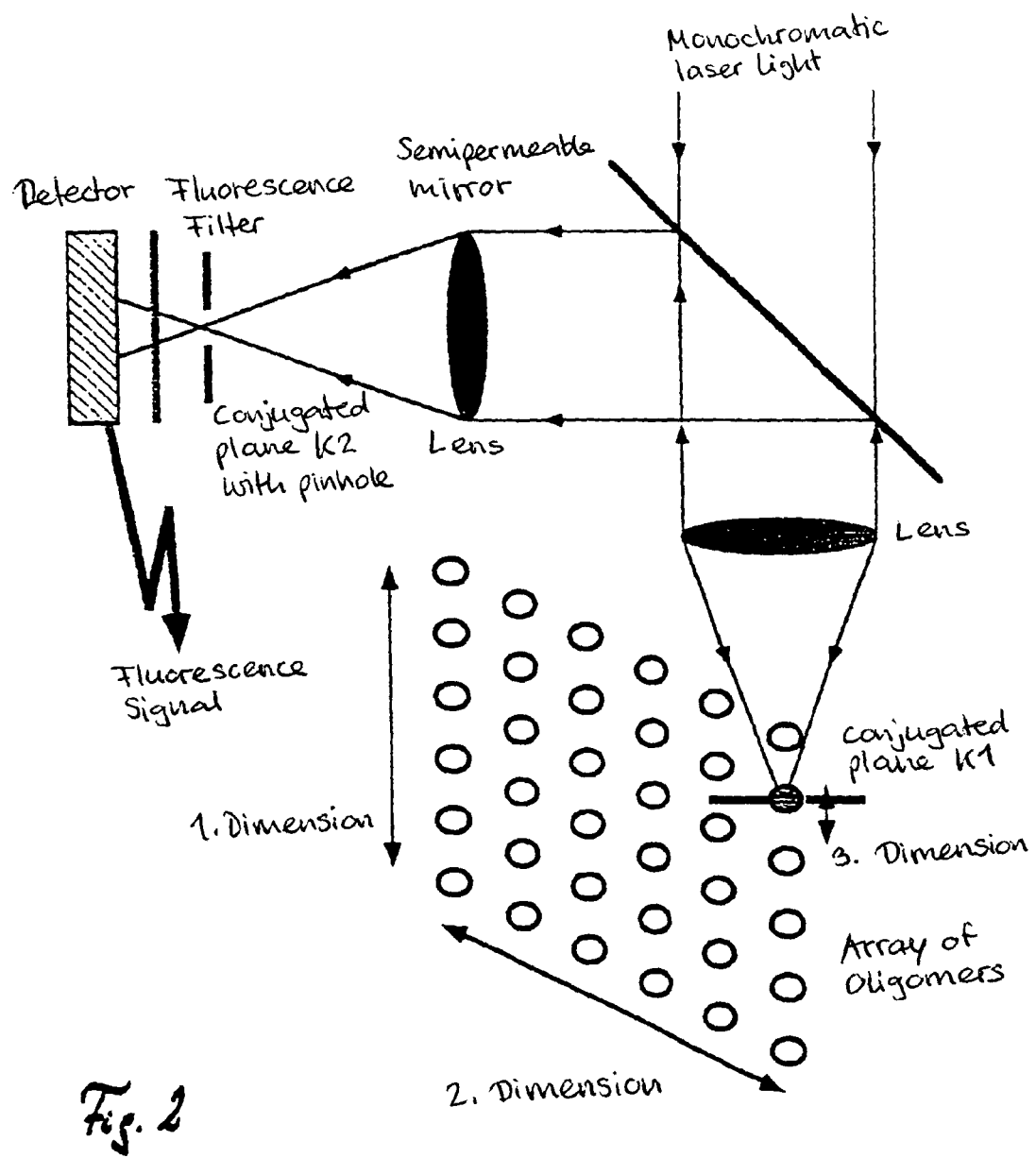

FIG. 2 shows the principle of the confocal laser microscope which is used for readout in the current, especially lithographic methods of synthesis. It can be seen that in this readout mechanism every single point of the array must be searched in all three dimensions which either costs time or accuracy.

Lithographic methods are known for applying molecules to the appropriate supports, especially to so-called "diagnostic chips" (FIG. 3) whereby however, as in the later investigation, the difficulty of exactly assigning molecules and reproducibly purposefully activatable support positions limits the maximum number of molecules which can be applied, since it is not sufficient to arrange very many different molecules closely packed on a support without knowing, however, with reproducible accuracy which molecules are located in which position on the support. In particular, in the known methods and devices reading out very many luminescence reactions on a support in a reasonable time and at the same time very accurately is a problem. In the staining investigations which can be carried out advantageously using the methods and devices with which we are concerned here, in which a material to be examined is applied to a support on which different molecules have already been anchored, conclusions should be reached on the substances present in the material to be examined, such as for example specific antibodies in a blood serum, with which the molecules of the material or its constituents anchored on the support have formed bonds so that one must know very accurately which molecule is located where on the support.

In addition, all known lithographic methods (and some other methods where, for example, locally precise synthesis is achieved by the controllable repulsion or attraction of electrically charged monomers) have another fundamental disadvantage: for each of the different monomers almost the entire linking cycle must be run through separately, i.e. each type of monomer is applied, linked and excess monomers washed away, followed by the next type of monomer so that, for example, in the combinatorial peptide synthesis layer for layer 20 linking cycles must be run through in each case. This disadvantage is shown schematically in FIG. 4. Thus, for the synthesis of a complex pentapeptide library these methods require 100 linking cycles whereby the expert can immediately appreciate that at the present state of technological development this will lead to serious quality problems for the resulting molecule libraries as a result of the artefacts to be expected in each linking cycle so that pentapeptide libraries produced in this way are in fact unusable.

This is also the reason why the lithographic methods have so far been used almost exclusively for the synthesis of oligonucleotide arrays since in this case only four different monomers need to be linked to the support.

Another side effect is the comparatively poor yield of chemicals in the lithographic methods since for each linking reaction the entire support must be covered uniformly with the reactive monomers.

Figure 5:
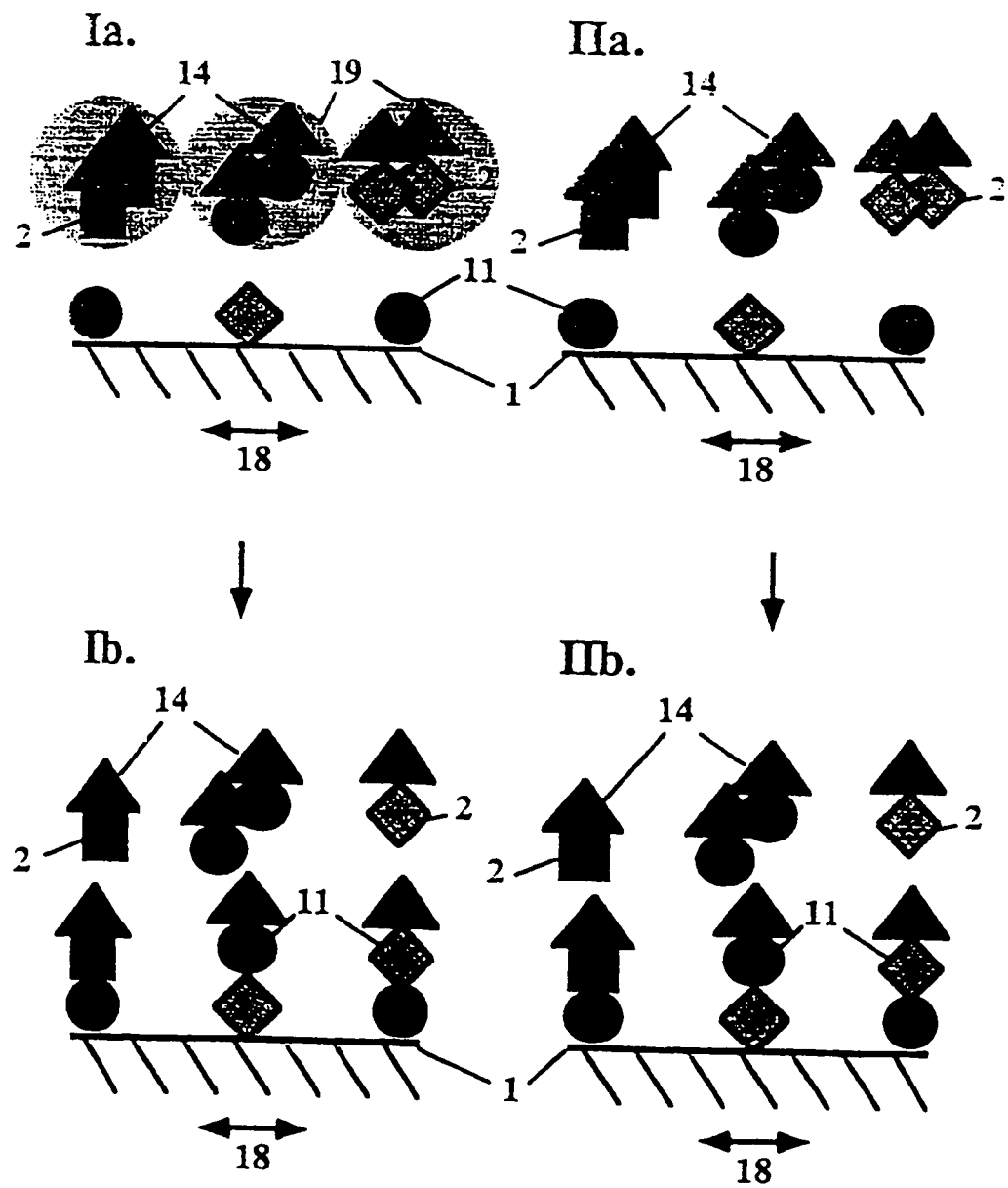

In addition to the lithographic methods, there are also many printing methods which can be used to carry out combinatorial syntheses (FIG. 5, IIa & IIb). So far however, none of these methods reaches the high resolution of the lithographic methods. The reason for this is mainly the high rate of diffusion of the relatively small monomers in solution. Since a certain time is always required both for the linking reaction of the monomers to the support and for the application of the monomers to the support in precise positions, the high diffusion rate thus limits the attainable compactness of the molecule libraries produced by combinatorial synthesis and therefore also their complexity.

A comparison with a normal color ink jet printer should clarify this argument (FIG. 6): the brilliance of the color imprints of color ink jet printers is achieved by keeping the diffusion of the various color particles as low as possible. This is achieved by the enormous size of the color particles compared with the afore-mentioned monomers and by the printed toner fluid containing rapidly volatile substances so that the color particles are precipitated very quickly. In addition, special highly absorbent high-gloss paper is used.

These papers generally having a complex structure are not usually suitable as supports for a molecule library and also the two other points are not consistent with the requirements for linking a molecule library as closely packed as possible to the support:

1. The monomers for combinatorial synthesis are very much smaller than the normally used color chromophores of a color ink jet printer and this fact alone increases the diffusion rate enormously.
2. Not only can the printed monomers not be dissolved in highly volatile solvents. It is barely even feasible to find a solvent that does not vaporise too rapidly in the desired quantities in the nanoliter range since the concentrations of the linking partners would thus change in an undesirable fashion because the linking reaction to the support (and the application of the monomers to the support in precise positions) requires a certain time.

This is the reason why all the spot methods used so far are liable to error and expensive as soon as they are used in smaller dimensions. In these dimensions there is always the risk that the applied spots run, the monomers diffuse too far or the solvent volatilises partly or completely.

It would therefore be desirable and advantageous to provide a method and a device to obviate prior art shortcomings in the synthesis of molecule libraries on supports.

SUMMARY OF THE INVENTION

In one aspect of the present invention, a method is provided for applying substances to a support, more especially monomers for the combinatorial synthesis of molecule libraries, wherein the substances (2) are first embedded in a matrix (3) includes at least one solvent (4), that at a temperature of <90° C., preferably at a temperature of <50° C. exists in the solid state of aggregation (7), wherein the substances (2) embedded in the matrix (3) including at least one first solvent (4) form transport units (5) which are moved (6) as units, wherein the transport units (5) are then applied (6) to the support (1) at a temperature of <90° C., preferably at a temperature of <50° C. in the solid state of aggregation (7), or that said transport units (5) are dissolved by a second solvent component (12) and at said temperatures are applied (6) to the support (1) in the liquid state of aggregation (13) where, after the complete or partial vaporisation of said second solvent component (12) they take on a solid or gel-like state of aggregation (7), wherein the transport units (5) remain in a solid or gel-like state of aggregation (7) after application to a support (1), wherein the substances (2) dissolved in the first solvent, which are located on the support (1), are then mobilised (9) by modifying the physical environment (8), more especially within said first solvent (4), wherein the substances (2, 9) thus mobilised enter the vicinity of the support surface (10) by means of a physical process, wherein the substances (2, 9) thus mobilised link covalently to molecules located on the support (1), or enter into a chemical reaction with these or catalyse these, wherein the substances (11) thus mobilised and linked covalently to the support are or yield many different substances (2), wherein more than one layer of said substances (2) is applied repeatedly one after the other to the support (1) in precise positions, in each case followed by the covalent linking of the substances to the support (11) and washing away non-linked substances.

The present invention resolves prior art problems by a method for the parallel synthesis of highly complex molecule libraries, which is characterised in that the monomers used for the combinatorial synthesis before or after transfer to the support are dissolved in a first solvent that is present in a solid state of aggregation below −5° C., preferably below +20° C., and has a vaporisation point of >100° C., preferably >150° C. Another characteristic of the method is that said solid state of aggregation is preferably converted within a short time back into liquid, preferably gel-like, state of aggregation, by supplying energy or by supplying a second solvent during the actual linking reaction of the monomers to the support.

As a result
1. The diffusion of the monomers is significantly limited and
2. said first solvent used is prevented from vaporising partly or completely during the application of the monomers or during the linking reaction.

This is particularly important if the application of the various monomers to the support in precise positions takes a fairly long time, which is the case, for example, when highly complex peptide libraries are to be produced with the aid of an ink jet printer by combinatorial synthesis of various amino acid derivatives.

The method can be executed advantageously such that in a repetitive process said particles or substances are repeatedly applied to the support in precise positions, in each case followed by the mobilisation of the immobilised substance described above, linking the substance to the support, washing away the non-linked substance and detaching the temporary protective group. If a modified color laser printer or color laser copier is used, it can be advantageous if the support remains fixed to the support roller or the transfer roller of the printer or copier throughout the entire repetitive process.

Instead of a single laser, an array comprising a number of purposefully controllable light sources, especially an array of microlasers, can naturally also be used. As a result of the action of the electromagnetic waves on the particles or the supports, these are electrostatically charged or heated in precise positions which brings about the locally precise transfer or locally precise fixing of said particles.

If the particles contain preliminary stages of monomers, dimers or trimers suitable for a combinatorial synthesis, the molecules bound to the support can be lengthened by further monomers, dimers or trimers by means of one or several further cycles of linking reactions. It is also possible to modify the molecules bound to the support by means of one or several more cycles of not necessarily identical reactions. Following successful synthesis the protective groups can be detached from the synthesised oligomers whereby the synthesised molecules remain bound to the support.

The particles and/or the immobilised substance can be melted or dissolved by a second substance or brought into a gel-like state.

It can be advantageous to mobilise said immobilised substance by the action of electromagnetic waves, especially laser light, or by applying an electrical voltage or by supplying thermal energy or by supplying a solvent. The mobilisation of the immobilised substance can thereby be limited to selected regions. Substances which have not been mobilised or not linked can be washed from the support using a solvent, preferably a heated solvent, or mechanically removed from the support with the aid of a stream of air.

Various materials can be used as supports. In particular, polystyrene films, paper, CDs, MODs, DVDs or FMDs can be used.

The supports manufactured by the method according to the invention can be used in a variety of different ways in scientific, especially medical research. For this purpose the support is usually brought in contact with the fluid to be examined. This fluid can, for example, be blood, blood serum, urine, faeces, lymph, saliva, amniotic fluid, gastric juice, vomit, sweat, seminal fluid, breast milk, lacrimal fluid, fluid containing an antibody or an extract from said fluids. If the fluid to be examined is a blood serum, this can be advantageously brought in contact with a specific detection reagent for immunoglobulin, especially for one with immunoglobulin of the type IgE, IgM, IgG or IgA. It is also possible to bring the support in contact with DNA to be examined. If DNA or a fluid containing an immunoglobulin are to be examined, it is advantageous if the fluid to be examined or the DNA to be examined are brought in contact with a material reacting with immunoglobulin or with DNA, especially forming linkages, before or after being brought in contact with the support. Before being brought in contact with the fluid to be examined or the DNA to be examined, this material reacting with immunoglobulin or DNA can be stained with a material excitable to luminescence and/or linked to another material which can produce luminescence, thus especially with an enzyme or a preliminary stage of a luminescent material. Said other material can advantageously be an enzyme, especially horseradish peroxidase, alkali phosphatase, beta galactosidase, glucose oxidase, lactate dehydrogenase or luciferase, or a linkage of enzymes.

As material excitable to luminescence it is more appropriate to use a dye excitable to fluorescence as a result of irradiation by electromagnetic waves, especially laser light or light from light-emitting diodes.

The research results obtained in this way can be used to advantage for the systematic classification and segmentation of pathological samples, especially to determine diagnostic markers in which said methods of examination are conducted for many test persons and deviations from the normal distribution present in the test results are determined.

For example, it is possible to take a blood serum sample from every test person and examine them using one of said methods. The deviation from the normal distribution can be determined, for example, for test persons who before or after blood serum was taken, suffer from cancer, especially paricular types of cancer, Parkinson's disease, multiple sclerosis, Alzheimer's disease, an infectious disease, an autoimmune disease, especially Crohn's disease, or had suffered a heart attack or stroke or had been or were becoming allergic.

The test results obtained in this way can be classified automatically in order to determine diagnostic patterns in which the signals are brought into relationship with structural parameters of the corresponding molecules in the molecule library so that correlations can be found, especially correlations which make it possible to obtain a diagnostic assessment of patterns of unknown samples. It is also possible to search for correlations which can be used to determine structural features of the discovered molecules found. The structural features of the discovered molecules thus defined can be used as guide structures for the development of functionally homologous other molecules, especially molecules having therapeutic applications. A peptide array that covers known human gene products by overlapping peptides can thereby be used to advantage.

In an additional method said monomers for combinatorial synthesis are incorporated in 0.2 µm to 200 µm, preferably 2 µm to 40 µm monomer-toner particles which at room temperature take on the solid state of aggregation. The term room temperature describes a temperature range between −10° C. and 80° C., but preferably between 0° C. and 40° C. Another characteristic of these particles is that with said first solvent they contain an inert constituent relative to the linking reaction, whose state of aggregation can be modified as described above. Preferably said particles also contain magnetic constituents or bind to particles which contain magnetic constituents. In FIG. 7 such a monomer toner particle is compared schematically with a normal chromophore toner particle.

The locally precise transfer of particles to the support is then accomplished using a largely commercially available laser printer (FIG. 8) or laser copier, more especially a color laser printer (FIG. 9) or color laser copier, whereby the laser responsible for transferring the particles, especially in the case of a laser copier, can also be replaced by a one- or two-dimensional array of microlasers.

The monomers applied in precise positions are then transferred from the solid state of aggregation to a liquid, preferably gel-like state of aggregation, as described above, whereby a locally precisely defined linking reaction is set in motion.

By this means, compared with the present state of technological development, a substantially more compact configuration of molecules produced with the aid of combinatorial synthesis is achieved very simply on a support and thus highly complex, comparatively artefact-free molecule libraries are produced.

Figure 10:
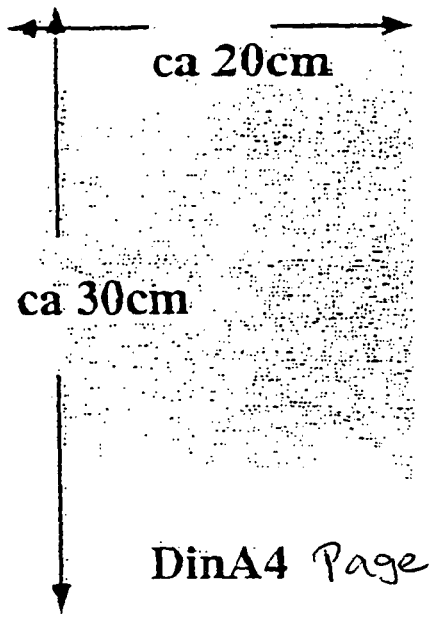

The technical characteristics of a laser printer should clarify this argument still further:

Commercially available laser printers have a resolution of printed points of 600 dpi (dots per inch). This corresponds to a diameter of individual printed pixels of approximately 40 µm or such a laser printer puts approximately 4500×7000 points per DIN A4 page (approx. 20×30 cm) in each normal printing process. This again corresponds to approximately 30 million points per DIN A4 page (FIG. 10).

FIG. 11 shows that this high resolution in a normal printing process using normal toner can be "harvested" almost error-free and reproducibly. In fact, the largest magnification of FIG. 11 shows no single wrongly set pixel.

Thus millions of spots can be accommodated on a DIN A4 page such than they can be identified separately. However, this is certainly nowhere near the end point of a clearly rapidly-developing technology. The laser printers now on the market having a resolution of 2,400 dpi put approximately 500 million pixels per DIN A4 page, with which very many more spots can be accommodated separately on a DIN A4 page.

Figure 12:
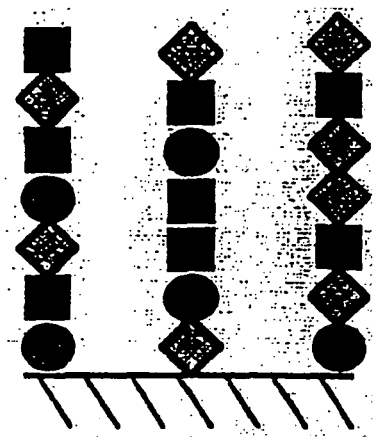

Thus, the commercially available laser printers are moving towards the numerical dimensions which make the combinatorial synthesis of hexapeptide or pentapeptide libraries with all possible representatives a possibility. The relevant numerical quantities are shown in FIG. 12.

In an alternative additional method said monomers for combinatorial synthesis in keeping with known technological developments are applied in the liquid state of aggregation in precise positions on the support, for example, with the aid of an essentially commercially available ink jet printer or other printing method.

For this purpose a solvent mixture is prepared to which are added, in addition to said monomers for combinatorial synthesis and said first solvent (for example, diphenyl formamide), at least one second solvent (for example, N-methyl pyrrilidone, dichloromethane, dimethyl formamide, methanol or isopropanol) which transfers said components at room temperature from the solid state of aggregation to the liquid state of aggregation (i.e., dissolves them). The term room temperature describes a temperature range between –10° C. and 80° C., preferably however between 0° C. and 40° C.

Another characteristic of said solvent mixture is that at room temperature said second solvent is highly volatile compared with said first solvent, i.e., the vaporisation point of both said solvents differs from one another by >80° C.

The evaporation of part of said second solvent thereby has the effect that said first solvent together with the monomers dissolved therein is first concentrated for the combinatorial synthesis and then transferred from the liquid state of aggregation back to the solid or gel-like state of aggregation without the monomers being able to move far from the original place of application as a result of diffusion. Said support is preferably kept at a temperature >10° C. lower than the storage container containing said solvent mixture. The barely volatile solvent fraction can be applied completely or partly to the support before said mixture is applied in precise positions. The solvent used must be inert in relation to the linking reaction.

The monomers applied in specific positions are then transferred from the solid state of aggregation to a liquid, preferably gel-like state of aggregation as described above, whereby a locally specifically defined linking reaction is set in motion.

By this means, a comparatively more compact configuration of molecules produced with the aid of combinatorial synthesis is achieved on a support and thus the production of highly-complex, comparatively artefact-free molecule libraries compared with technological developments so far.

The invention includes devices with which monomers for the combinatorial synthesis of support-bound molecule libraries can be applied in precise positions. The linking of the individual layers of applied monomers is accomplished as described above.

Said monomers are bound in particles as described below.

The locally precise transfer of said particles onto the support is then achieved using a device (FIGS. 13 and 14) which is essentially based on a commercially available laser printer or laser copier, especially a color laser printer or color laser copier. The laser responsible for transferring the particles, especially in the case of a laser copier, can also be replaced by a one- or two-dimensional array of microlasers.

The following modifications distinguish said device from said commercially available laser printers or laser copiers.
1. Instead of the usual toner particles, particles containing said monomers are used as described below.
2. Not merely a single layer of monomer particles is applied but several layers of particles containing said monomers are printed one on top of the other.
3. In each case, between applying said several layers said monomers are linked to the support, unlinked monomers are removed from the support and the temporary protective groups are detached from the support-linked monomers.
4. Before applying the last layer of said monomers, the support remains in an exact spatial relationship relative to the laser responsible for transferring the particles, where it is sufficient if this spatial relationship is reproducible. By this means said layers and said various monomer particles within the layers can be placed in precise positions above each other or next to each other. Said spatial relationship can be produced via a feedback mechanism (FIG. 14) and/or by exact mechanical linkage (FIG. 13) between the support roller or the transfer unit and the laser-ionisable roller. Both methods can naturally also be combined.

Figure 14:
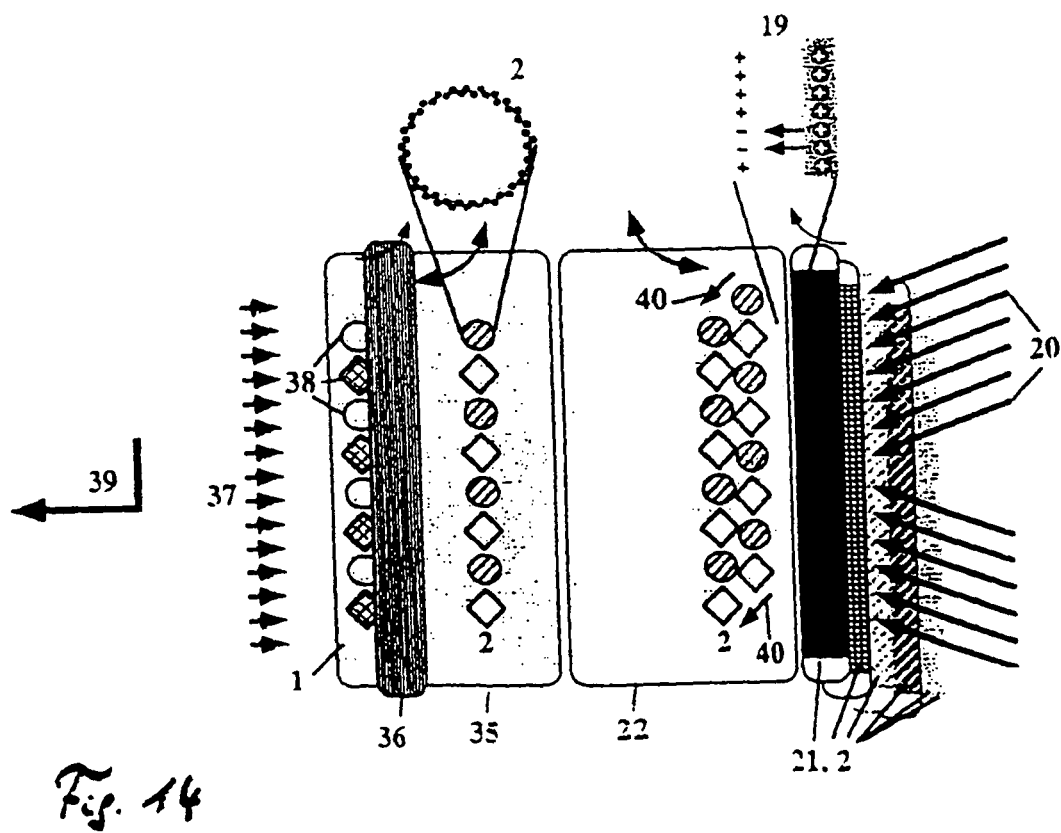

For example, a grid of position markings (FIG. 14, 38) can be applied to the support or to the support roller (35), which is read by a scanner line (FIG. 14, 37) and compared with a stored grid (FIG. 14, 39). Electronic displacement of the pixels in the printer memory exactly by the amount of the measured deviation (FIG. 14, 40) is then part of said feedback mechanism.

The invention includes materials produced according to the invention. These include monomer-toner particles which can be applied in precise positions on the support by said device which is based on an essentially commercially available laser printer or laser copier. These monomer-toner particles differ from the commercially available toner particles as follows:

1. Instead of the chromophores, the monomer-toner particles contain suitable monomers or their derivatives for combinatorial synthesis, more especially also pre-activated monomers.
2. Instead of or in addition to a meltable plastic component (e.g. polystyrene), the monomer-toner particles contain an inert solvent in relation to linking of the monomers to the support (e.g. diphenyformamide) which takes on the solid state of aggregation at room temperature. The term room temperature describes a temperature range between −10° C. and 80° C., preferably however 0° C. to 40° C.

Other characteristics of said monomer-toner particles are:
3. Their size is between 0.2 μm and 200 μm but preferably between 2 μm and 40 μm in diameter.
4. Said monomer-toner particles take on the solid state of aggregation at room temperature. The term room temperature describes a temperature range between −10° C. and 80° C., preferably however 0° C. to 40° C.
5. Another characteristic of said monomer-toner particles is that they contain magnetic constituents or bind to particles which contain magnetic constituents.

Other materials produced according to the invention include monomer-toner fluids which can be applied to the support in precise positions using an essentially commercially available ink jet printer or color ink jet printer.

These monomer-toner fluids differ from the commercially available toner fluids as follows:
1. Instead of chromophores, these monomer-toner fluids contain suitable monomers or their derivatives for combinatorial synthesis, more especially also pre-activated monomers.
2. In addition to a first solvent component which is liquid at room temperature (e.g. isopropanol, dimethyl formamide, N-methyl pyrrilidone, dichloromethane), the monomer-toner fluids contain at least one second inert solvent in relation to linking of the monomers to the support (e.g. diphenyl formamide) which takes on the solid state of aggregation at room temperature. The term room temperature describes a temperature range between −10° C. and 80° C., preferably however 0° C. to 40° C. Said second solvent is thereby dissolved by said first solvent at room temperature.

A characteristic of the first solvent is that its melting point and its vaporisation point are more than 40° C., preferably more than 70° C., lower than the melting point and the vaporisation point of the second solvent.

A characteristic of the first solvent is that below −80° C., preferably below −20° C., it occurs in a solid state of aggregation and that it has a vaporisation point of >40° C., preferably >70° C.

A characteristic of the second solvent is that below −5° C., preferably below +20° C., it occurs in a solid state of aggregation and that it has a vaporisation point of >200° C., preferably >250° C.

A characteristic of the mixture of said at least two different solvents together with the monomers dissolved by them is that below −20° C., preferably below 0° C., the mixture occurs in a solid or gel-like stage of aggregation.

Other materials produced according to the invention include the molecule libraries produced using said method, materials or devices, especially peptide or oligonucleotide libraries. A characteristic of these molecule libraries is:
1. that they are produced by the combinatorial synthesis of a limited number of monomers,
2. that they occur as a two-dimensional array on a suitable derivatised support whereby the individual constituents of the molecule libraries can be assigned locally precisely. The derivatisation of the support is carried out in keeping with technological developments known to the specialist.

As supports for molecules, especially biological molecules, more especially for use in one of said methods it is possible to use supports according to the invention which have a fine-meshed network of integrated position markings so that the position of a place to be examined, applied to the support by means of conventional mechanics, can be monitored with a detector. Preferably the position markings should be constructed so that they can be detected by an optoelectronic scanning system.

The invention thus creates completely new diagnostic possibilities and in particular increases the chances of finding diagnostic markers and therapeutics. For example, if complete 6-mer peptide libraries are brought in contact with a fairly large number of patient sera and, for example, examined by means of a staining reaction to determine on which peptides serum constituents have deposited, correlations will be obtained between disease and stained peptides. This is because every person carries an extremely complex individual pattern of antibody reactivities in their blood serum which in particular mirrors the conflict of their immune system with acute, chronic or hidden diseases or diseases which have already been overcome. A large proportion of the antibody reactivities can be defined by specific binding to penta- or hexapeptides whereby in analyses of the binding reactivities to a complete penta- or hexapeptide library the afore-mentioned individual pattern of antibody reactivities can be determined in as yet unknown complexity.

So-called complete peptide libraries are explained in FIG. 15. Each locally precisely defined spot of an array of such a complete peptide library represents a peptide mixture which only carries a different in each case, defined sequence at the sites per spot denoted by N. The reason for working with this peptide mixture is that in an antibody-peptide antigen reaction the recognised peptide antigen requires a certain size so that it can be specifically recognised by the antibody. However, since at the present state of technological development it is not possible to produce a complete decapeptide library with $20^{10}$ different members, said mixtures are used.

Figure 16:
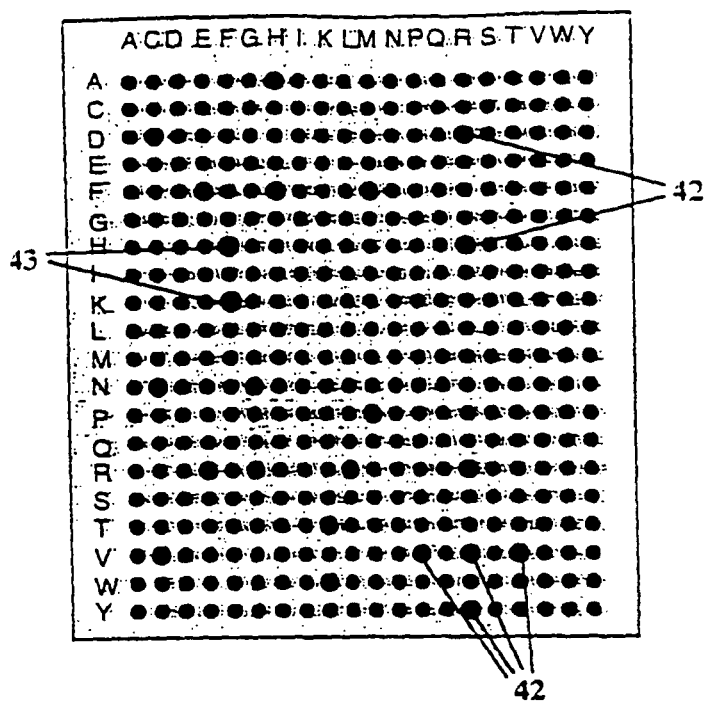

An advantageous usage of such an array is shown schematically in FIG. 16 (see also Example (1.)). The differential staining of a highly complex array of peptides with control serum and serum from patients gives, on the one hand, reaction partners (and thus peptide sequences) recognised by both sera (FIG. 16, 42) and on the other hand, peptides which are specifically recognised by patient sera (FIG. 16, 43). This makes it possible to identify patient-specific staining patterns. In the given example (FIG. 16 and Example (1.)) peptides are identified (FIG. 16, 43) which correspond to expressed gene products of Helicobacter pylori, which causes gastric ulcers. This means that disease and peptide pattern can be intercorrelated with the aid of such an array.

In addition to determining epitopes of monoclonal antibodies, said complete peptide libraries are also suitable for tracing diagnostic markers by the correlation of the serum profile with the diagnosed disease, for example, autoimmune diseases or allergies (e.g. rheumatism, hay fever, asthma, food allergies, Lupus erythematosus, juvenile diabetes etc.), infectious diseases (e.g., influenza, influenza-like infections, AIDS, hepatitis, measles, mumps, meningitis, gastric ulcers, malaria, Chagas disease etc.), cancers (e.g. lung cancer, liver cancer, bowel cancer, carcinoma of the kidneys, breast cancer, prostrate cancer, glioblastoma, lymphoma etc.), and especially diseases of unknown or doubtful origin (e.g. heart attack, stroke, Parkinson's disease, multiple sclerosis, Alzheimer's disease, Crohn's disease, Creutzfeld-Jacob disease etc.).

In addition, this method is not limited to a single disease but very many diseases can also be diagnosed in parallel, or conversely as yet unknown causes of disease can be traced using the identified peptides.

Last but not least said arrays are also suitable for searching for interaction partners, for example, of human or viral gene products with which in this case said complete libraries can be stained. For example, by staining with purified virus particles one or several binding motives could be identified very rapidly and by comparing the corresponding peptide sequences with the human peptide sequences filed in the data bases the entry point of the virus into human cells could be identified.

Longer binding motives, especially those occurring frequently having a helical structure, can be determined by libraries in which not every amino acid is random but only those at certain positions derived from the structure. By this means new diagnostic markers and as yet unknown correlations can be found between disease and specific antibody reactivities, including for example, markers for tumour diseases, cardiovascular diseases such as heart attack, for multiple sclerosis and Parkinson's disease, for all types of autoimmune diseases and allergies and for all types of infectious diseases.

The pattern of markers obtained can on the one hand be used itself to make a diagnostic prediction by means of the correlation to certain clinical pictures. But the newly found markers can also be applied separately to supports and used in future research.

The same also applies to the use of so-called unigene product arrays. The human possesses approximately 100,000 genes which on average code approximately 500 amino acids. In a few years more than 90% of these genes will be known. If each of these gene products is covered by an average of 100 overlapping 15-mer peptides, which are each displaced relative to each other by five amino acids, approximately 10 million different peptides will be needed to cover all human gene products. Such an array is shown schematically in FIG. 17.

Intermediate goals may also take the form of expression arrays which each only cover one part of the human gene products, e.g. "oncogene arrays", "immunology arrays" etc.

As described above for the complete peptide libraries, these arrays are especially suitable for analysing the serum antibody profile of autoimmune patients (see above). Particularly clear signals are to be expected since an array with individual defined and relatively long peptides appears here.

These arrays are also especially suitable for analysing serum from patients suffering from illnesses of as yet unknown causes. These arrays can, for example, answer the question as to whether multiple sclerosis or Parkinson's disease or various cancers have an autoimmune component. Conversely these arrays are especially suitable as diagnostic tools for said diseases.

As described above, the arrays can also be used in the search for interaction partners and thus, for example, to help answer the question as to which human gene products are the entry point for particular virus particles.

Similarly, attempts can also be made to correlate diseases to binding patterns to other molecular libraries such as D-peptide libraries or oligosaccharide libraries. This method is not restricted to human diseases but is also suitable for examining forensic and veterinary medical questions as well as for analysing other fluids, from plant extracts to extracts from microorganisms.

In another application molecules of potentially therapeutic interest such as, for example, D-peptides, which cannot be broken down by human digestive enzymes are arranged on a support and then brought in contact with medically relevant molecules, especially pathogen-specific proteins or with mixtures of pathogen-specific proteins. This allows a specific and rapid search for binding partners to these medically relevant molecules. Similarly it is also possible to search for enzyme ligands, enzyme substrate analogues or enzyme inhibitors.

Finally, binding to medically relevant molecules can also be detected, for example, by way of biotinylation or fluorescence marking so that the D-peptides or aptamers can be identified which bind at least parts of the pathogens. These D-peptides or aptamers can then be tested one after the other to determine whether they inhibit the pathogens. For example, if an enzyme of the pathogen (e.g. HIV protease, reverse transcriptase etc.) is present in a suitable quantity, this enzyme can be fluorescence-marked (either directly or with the aid of an antibody or by the recombinant expression of a small peptide tag which can be stained using a monoclonal antibody). It can thus be determined to which D-peptide the enzyme has bound. Then another staining reaction is carried out which is caused by the enzyme activity. For example, cleavage by the HIV protease precipitates a fluorescent peptide that can be detected. Thus we obtain D-peptides which not only bind the enzyme but also inhibit at the same time.

Figure 18:
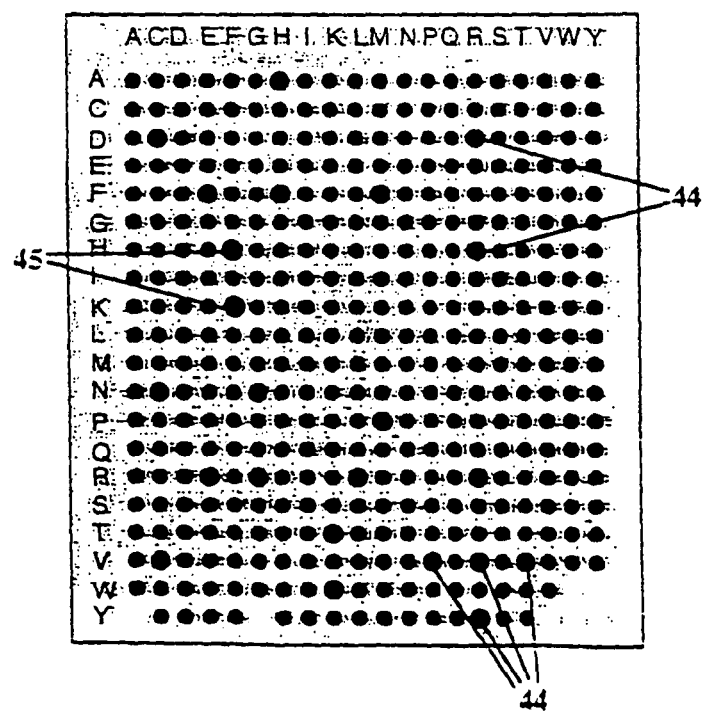

The advantageous usage of such an array is shown schematically in FIG. 18. This enables enzymes to be detected in two ways.

a. Identification of peptides which bind the enzyme (FIG. 18, 44) without blocking its enzyme activity and b. Differential identification of peptides which bind the enzyme and at the same time block its enzyme activity (FIG. 18, 45). The latter modules of D-peptides are especially suitable as building blocks for potential therapeutics.

In a next step binding modules having an inhibitory effect can then be lengthened by other monomers or combined with one another, followed by another detection of the inhibitory action.

In order to determine to which of the molecules bound to the support molecules have added on, after or before the support is brought in contact with the blood serum or the DNA, the blood serum or DNA can be brought in contact with a substance which reacts with the blood serum or the DNA, especially forming linkages. More appropriately. before being brought in contact with the serum or the DNA, the substance reacting with the blood serum or the DNA is stained with a substance excitable to luminescence, especially a substance excitable to fluorescence by exposure to laser light. Such dyes are available commercially, for example, under the names "Cy3", "Cy5", "FITC" or "TRITC" whereby a whole range of conjugates of these fluorescence dyes are already available advantageously (for example, goat-antihuman antibody conjugated Cy5).

If the blood serum to be examined is brought in contact with a detection reagent specific for type E immunoglobulins, it may well be possible to determine existing allergies in the patient since the type E immunoglobulins are responsible for allergic reactions such as asthma or hay fever. Non-allergy sufferers have almost no IgEs in their blood serum, allergy sufferers have different quantities which can reveal different allergens. Finally, the invention makes it possible to search for specific binding partners for a target molecule from a highly complex library and thus, by simultaneously identifying many (of varying binding strength) binding partners, to search for the structural parameters responsible for binding the ligands to the target molecule. By this means the path to guide structures is simplified substantially. For example, signal patterns obtained using the afore-mentioned methods can be automatically correlated with structural parameters or structural models of the identified ligands from the libraries used.

Said advantageous applications are by no means restricted to peptide arrays and the examination of blood serum. In addition there is an abundance of other possible applications when it is always advantageous to examine a large number of potential binding partners for binding. This particularly applies to the combination of two molecule libraries of which one library represents said arrays and said blood serum is only one example among many for such a second library. The binding partner is identified in said arrays on the basis of its position on the array whereas other advantageous methods of detection, such as mass spectrometry for example, can be used to identify the second binding partner.

DETAILED DESCRIPTION OF PREFERRED EMBODIMENTS

Subsequently, some examples of the implementation of the method according to the invention or the usage of the devices according to the invention are described with reference to the drawings.

The figures are as follows:
FIG. 1: Combinatorial synthesis:
I. Substances (2) suitable for combinatorial synthesis are applied to a support (1)
II. The various substances (2) are linked (11) to the support (1)
III. The non-linked substances (2) are washed away
V. The protective groups (14) are detached
V. More substances (2) are applied to the support (1) and the next cycle begins.

FIG. 2: The confocal laser microscope as readout principle for arrays
If arrays are to be evaluated using a confocal microscope, all three spatial dimensions must be searched until the desired signal can be uniquely identified. Compared with this a scanner, for example, is much quicker:
1. It has not merely one laser available but works in parallel with a one-dimensional array of light-emitting diodes.
2. Since the light from the light-emitting diodes penetrates almost parallel to the support, searching in the third spatial dimension is not necessary with the scanner.

Figure 3:
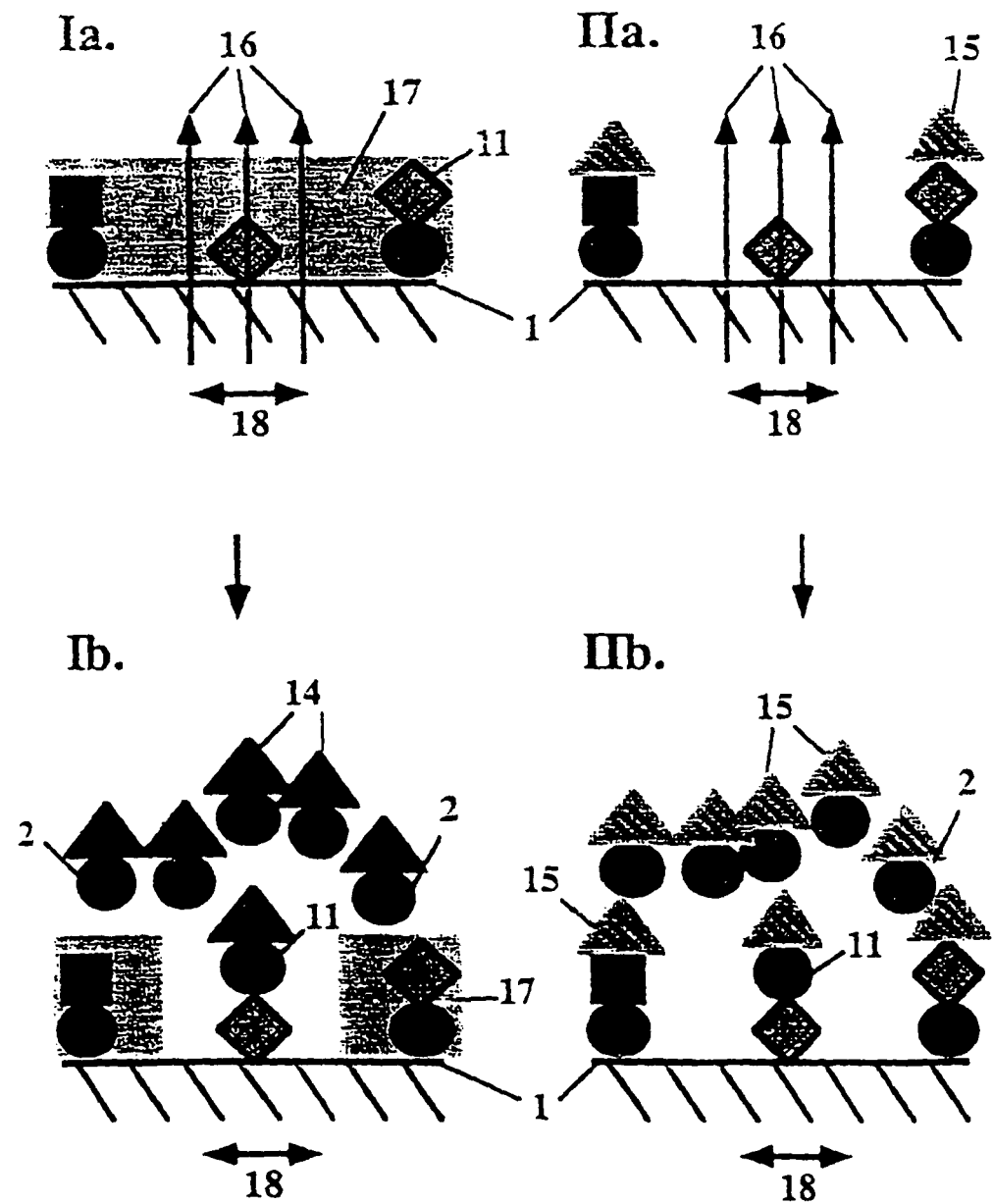

FIG. 3: Lithographic method for combinatorial synthesis. In the conventional lithographic methods of synthesis the synthesis site is made accessible for the activated monomers by the action of light (FIG. 3, I.) or light-sensitive groups are detached (FIG. 3, II), whereby a locally definable chain lengthening is made possible. An advantage of both methods is their high resolution. A disadvantage of both methods is that the entire synthesis cycle is run through one after the other for each monomer which is at the expense of quality.

Ia. After the action of light (16) a light-sensitive protective layer (17) can be removed in precisely defined positions (18).
Ib. By this means applied monomers (2) for the combinatorial synthesis can be linked (11) to the support (1) in precisely defined positions (18).
IIa. After the action of light (16) light-sensitive protective groups (15) are detached in precisely defined positions (18).
IIb. By this means applied monomers (2) for the combinatorial synthesis can be linked (11) to the support (1) in precisely defined positions (18).

Figure 4:
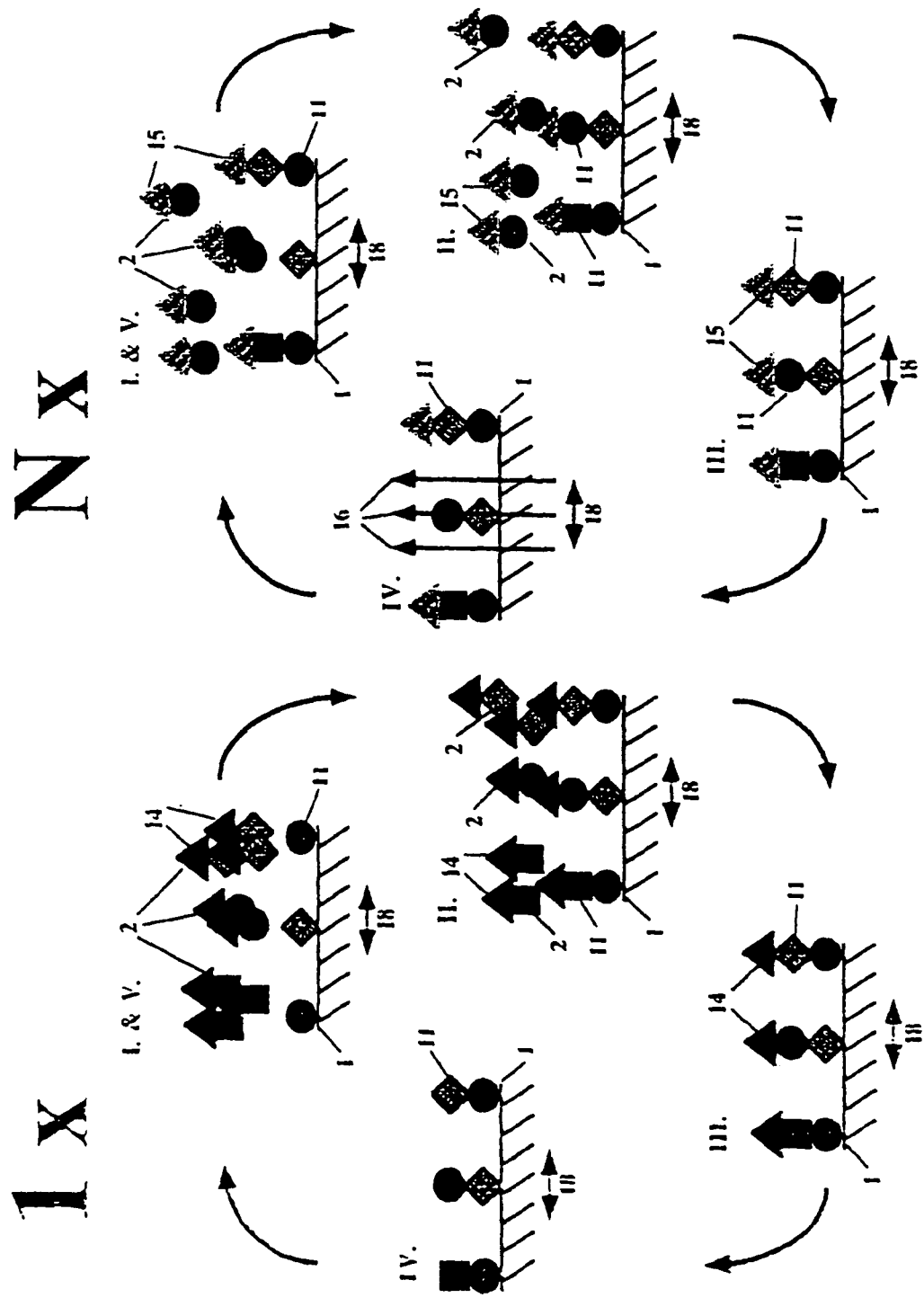

FIG. 4: Disadvantages of the lithographic methods of synthesis
In all printing methods an entire layer of various monomers (2) is always applied to the support (1) which all run through a linking cycle together before the next layer of monomers (2) is again printed on. In the lithographic method of synthesis shown in FIG. 3, however, each type of monomer (2) must be applied individually one after the other, linked (11) and excess monomers washed away. This means that for the synthesis of the same array of oligomers the lithographic methods of synthesis must run through Nx more linking cycles than is required for the printing process. The number N here stands for the number of different monomers (2), i.e., for the synthesis of an array of oligopeptides the lithographic syntheses required 20× more linking cycles compared with the printing method.

FIG. 5: Printing method for combinatorial synthesis.
Ia. Toner particles or transport units (19) containing substances (2) suitable for a combinatorial synthesis are applied in precisely defined positions (18) to a suitable derivatised support (1).
Ib. The monomers (2) for the combinatorial synthesis are then released from the toner particles or the transport units (19) and then link (11) to the support (1) in precisely defined positions (18).
IIa. Fluids containing suitable substances (2) for a combinatorial synthesis are applied to a suitable derivatised support (1) in precisely defined positions (18).
IIb. The monomers (2) for the combinatorial synthesis then link (11) to the support (1) in precisely defined positions (18).
IIa and IIb describe the printing method in keeping with technological developments used for the combinatorial synthesis. Ia and Ib describe the new method according to the invention. It combines the advantages of the printing methods with the advantages of the lithographic methods. Here also, as in the lithographic method, the high resolution of laser light is used to obtain closely packed molecule libraries. On the other hand, as in the other printing methods an entire layer of different monomers can thus be applied in parallel to the support.

FIG. 6: Disadvantages of monomer spotting
When paper is printed with ink, the printed chromophores must diffuse as little as possible since this would disturb the brilliance of the printed picture. This is achieved by the applied chromophores being fixed very rapidly on the spot as a result of highly volatile constituents in the toner fluids used. Moreover, the chromophores used are relatively large which considerably limits their diffusion rate. In addition, special highly absorbent high-gloss papers are used.
The applied monomers (for a combinatorial synthesis) will, however, diffuse very much further since the solvents used for the synthesis have very low volatility since time is needed to link the reaction partners. The monomers used are also comparatively small which appreciably increases their diffusion rate. Special papers are not normally suitable as supports for a molecule library.

FIG. 7: Schematic comparison of the particle of a normal toner (46, 47, 48) and an "amino acid toner" (46, 49, 2, 50):

The equivalent of the solid polystyrene bead (47) of the normal toner at room temperature is in this case diphenyl formamide (50) with a melting point of approximately 71° C.

The magnetic component (46) is in both cases contributed by magnetite particles.

Instead of chromophores the amino acid toner contains activated amino acids (49, 2) provided with an N-terminal protective group.

Figure 8:
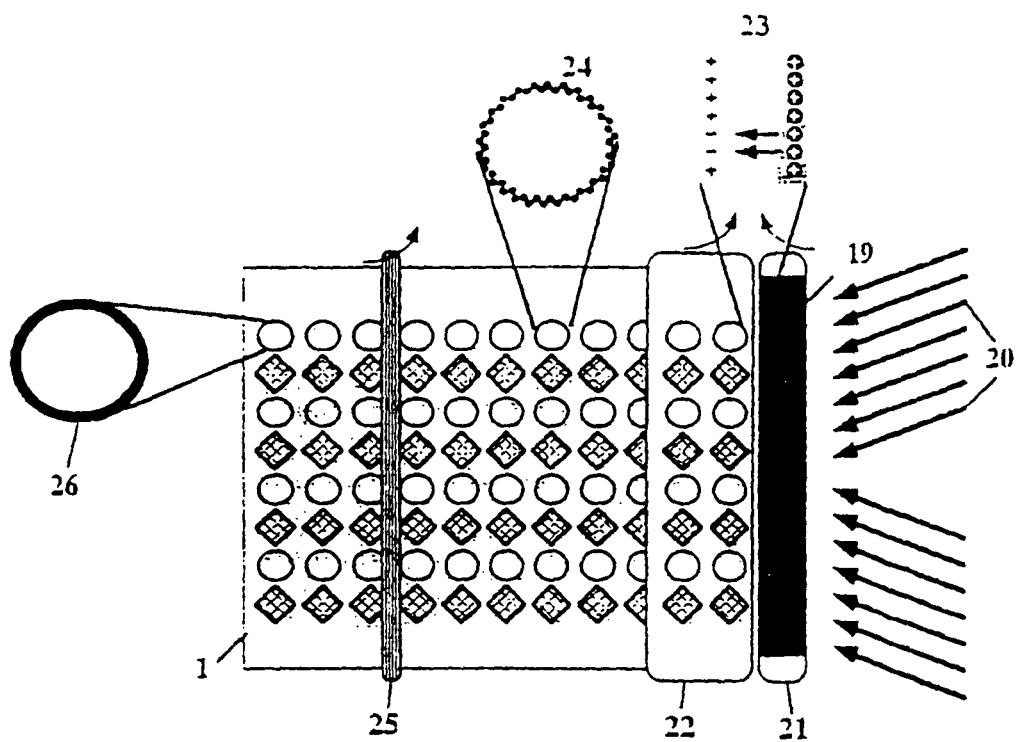

FIG. 8: Mode of operation of a laser printer:

Toner particles (19), consisting of small polystyrene beads with a magnetic component adhere to the magnetic roller (21) as a result of the magnetic component. There they become electrostatically charged and jump onto precisely defined regions of a laser-writable roller (22) as a result of this charge. These regions are defined by the laser which "writes" specific regions by switching on and off. As a result of electrical forces of attraction, the toner particles (19) jump (23) from the magnetic roller (21) onto the regions of the roller (22) written by the laser. From there the toner particles (19) jump onto the support (24) (e.g. paper or a copier film) and are fused by a hot roller (25) or in the case of amino acid toner particles the incorporated substances are mobilised (26).

Figure 9:
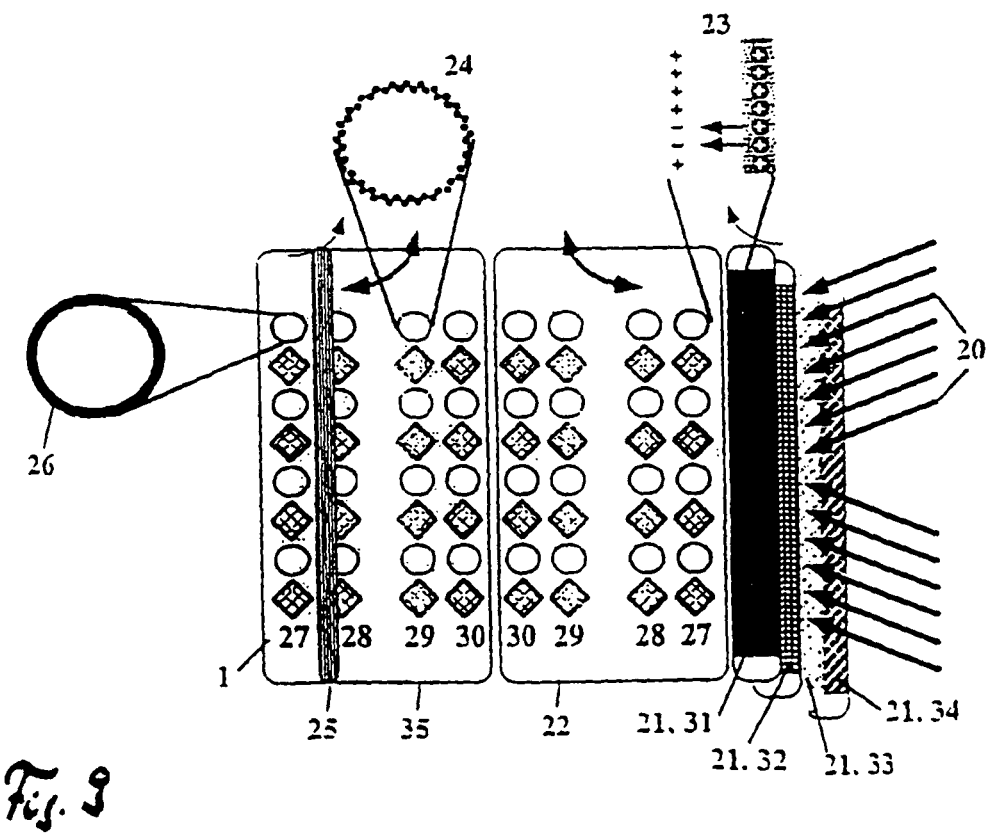

FIG. 9: Mode of operation of a color laser printer:

As for a black and white laser printer (FIG. 8), for a color laser printer the toner particles (20) consist of polystyrene beads and a magnetic component. They adhere to a magnetic roller (21) as a result of the magnetic component. There they are electrostatically charged and jump onto precisely defined regions of a laser-writable roller (22) as a result of this charge. The regions are defined by the laser which "writes" specific regions by switching on and off. As a result of the electrical forces of attraction the toner particles (20) jump (23) from the magnetic roller (21) onto the regions of the roller (22) written by the laser. From there the toner particles (20) jump onto the support (24) (e.g. paper or a copier film) and are fused by a hot roller (25) or in the case of amino acid toner particles the incorporated substances are mobilised (26).

Unlike the black and white laser printer (FIG. 8), a color laser printer must not only print a toner (20) but four different-colored (31, 32, 33, 34) toner particles (20) exactly next to one another.

A way of solving this problem is shown schematically in FIG. 9:

the laser-writable roller (22) is substantially larger than for the black and white laser printer (FIG. 8)

in this way the laser can "write" an entire sheet on this roller the laser "writes" the laser-writable roller (22) with the first color a magnetic roller (21) transporting the first color toner (21, 31) moves towards the writable roller (22)

from there the toner particles (21, 31) jump onto the "written" writable roller (22)

the writable roller (22) is closely mechanically coupled to an equally large second roller (35)

on this roller (35) a support (1) is applied and fixed there the two rollers (22 and 35) turn in opposite directions thus the first toner (27) is transferred to the support (1) which remains fixed on the roller (35)

the laser "writes" the writable roller (22) with the second color then other alternative magnetic rollers (21, 32, 33, 34) move towards the writable roller (22)

which transfer the other colors (28, 29, 30) to the writable roller (22)

from there the other colors (28, 29, 30) are transferred to the support (1)

and only when the entire printing process is completed is the support released

Instead of the support roller (35) a so-called transfer unit can be used which is continuously adjusted relative to the writable roller in a feedback mechanism.

FIG. 10: Commercially available laser printers have a resolution of 600 dpi i.e. the individual points printed by this device have a diameter of approximately 40 µm.

FIG. 11: A printed pattern of a commercially available laser printer with 600 dpi resolution was scanned using a commercially available scanner with 600 dpi resolution. Here the scanning of the scanned-in laser printed pattern typically shows no wrongly placed pixels at higher magnification.

FIG. 12: Complexity of combinatorial peptide libraries.

Figure 13:
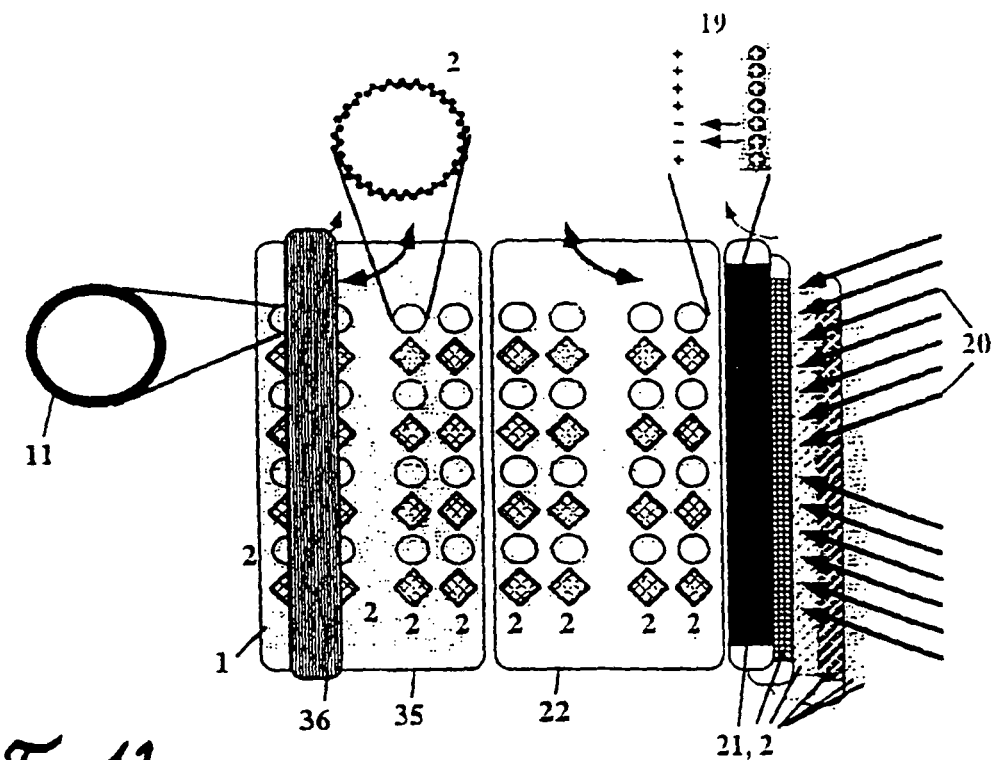

FIG. 13: Equipment for combinatorial synthesis.

Unlike the color laser printer described in FIG. 9, in this equipment the hot roller (25) has been replaced by a device (36) which can be used to bring linking reagents or washing solutions in the gaseous or liquid state in contact with the rotating support roller (35). Gaseous substances (also hot air) are supplied with the aid of a wide nozzle (36) whereas liquids, for example, are brought in contact with the support (1) of the molecule library fixed on the support roller (35) by means of an endless strip (36). A row of infrared light sources (36) can also be used to mobilise the substance (2). The alternative magnetic rollers (21) with four different-colored toners (31, 32, 33, 34) is exchanged for alternative magnetic rollers (21) with the 20 different amino acid toners (2, 19).

FIG. 14: Equipment for combinatorial synthesis with built-in feedback mechanism.

A scanner unit (37) scans a pattern (38) applied to the support (1) or the support roller (35) and compares it with the same previously stored pattern (39). If a deviation from the desired value is established, the image loaded into the printer memory is displaced (40) electronically by this deviation. By this means the transport units (19) or the substances (2) contained therein can be reproducibly printed next to each other or above each other in precise positions.

FIG. 15: Complete peptide libraries

Arrays of decamer mixtures shown can be synthesised on a support with the aid of the method described above. All possible combinations of amino acids denoted by N are covered by the array.

FIG. 16: Correlation of disease with peptide pattern

The differential staining of a highly complex array of peptides with control serum and patient serum yields, on the one hand, peptides (and thus peptide sequences) recognised by both serums (42) and on the other hand peptides recognised specifically by patient serum (43). This makes it possible to identify patient-specific staining patterns. In the given example, peptides are identified (43) which correspond to expressed gene products of Heliobacter pylori which causes gastric ulcers.

This method is not restricted to a single disease and can be used to diagnose several diseases in parallel or conversely as yet unknown pathogens can be traced using the identified peptides.

Figure 17:
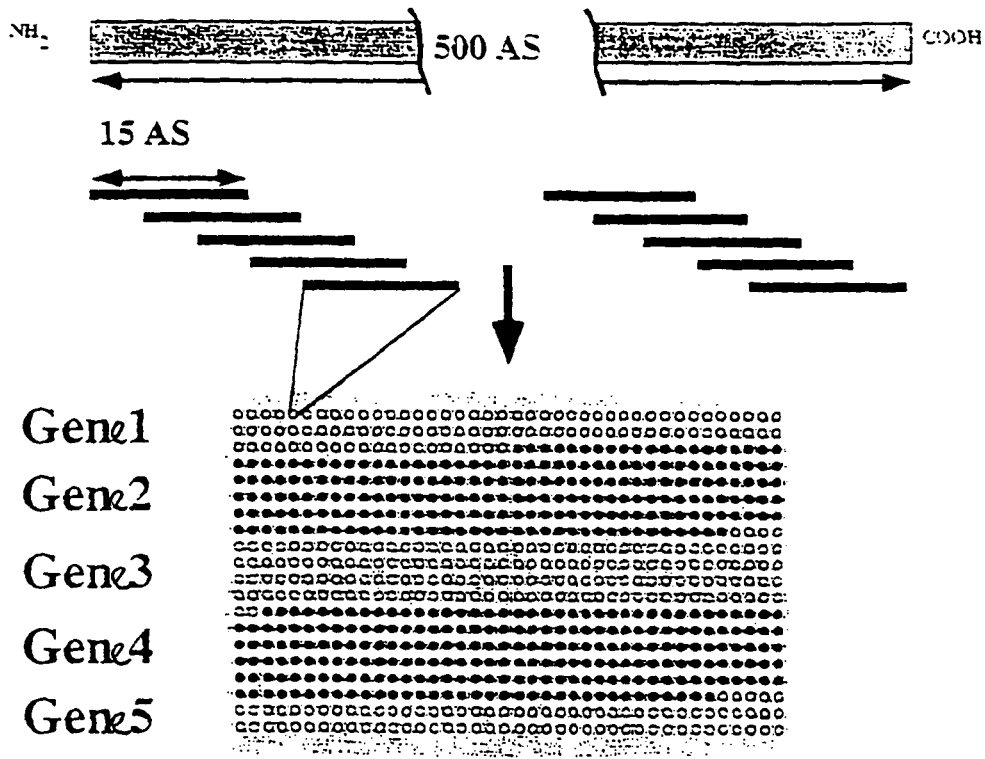
Figure 13:
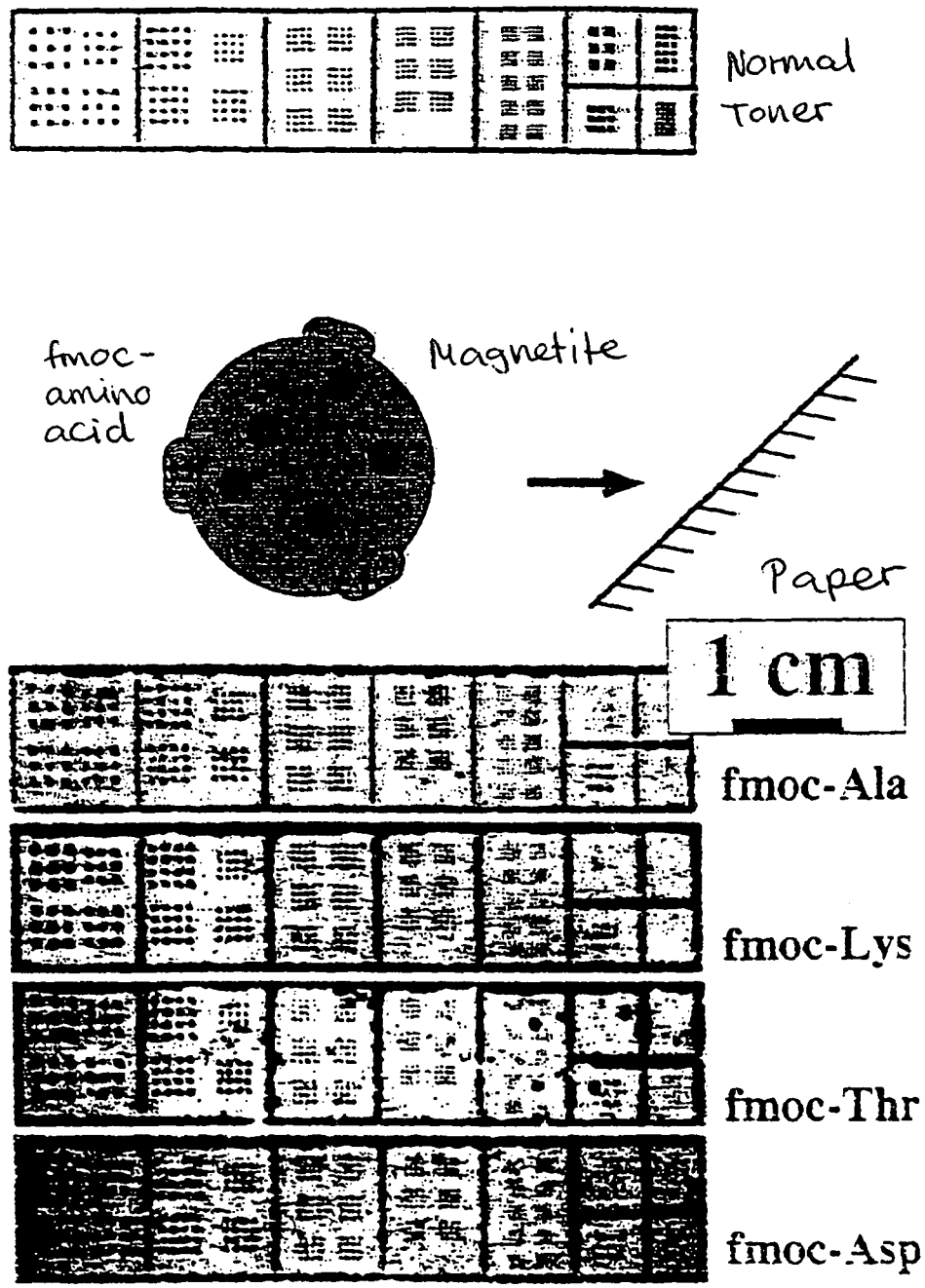

FIG. 17: Array of gene products, unigene product arrays
The approximately 100,000 human genes (i.e. the genome) code an average of somewhat less than 500 amino acids per gene. In a few years most of these genes will be known. Each of the corresponding gene products can be represented by an average of 100 overlapping 15-mer peptides which are each mutually displaced by 5 AS. In total then approximately 10 million different peptides are required to cover all 100,000 human gene products (i.e., its proteom).

FIG. 18: Search for enzyme inhibitors
Two different ways of detecting enzymes can be used:
  a. Identification of peptides which bind the enzyme (44) without blocking its enzyme activity.
  b. Differential identification of peptides which bind the enzyme and at the same time block its enzyme activity (45). These latter modules of D-peptides are suitable as building blocks for potential therapeutics.

FIG. 19: Comparison of print quality of normal commercial toners with various "amino acid toners":
The various toners were loaded in a toner cassette and printed with a laser printer on normal paper. The amino acid toners are colored by the magnetite particles contained therein.

FIG. 20: Lysine followed by asparaginic acid is successively linked uniformly to the free amino groups from derivatised paper. Then two different peptides are synthesised on one support from derivatised paper in a checkerboard fashion. In this way the amino acid toners corresponding to amino acids 1 to 10 shown in FIG. 20 are produced. The marked amino acids 1 to 5 in FIG. 20 are printed in a regular pattern of ovals 11 whereas the marked amino acids 6 to 9 are printed as a second pattern of regularly arranged rectangles 12. Both patterns intermesh in a checkerboard pattern. The N-terminal amino acid asparaginic acid is then linked again uniformly to the support in a last step, followed by detachment of the protective groups.
The synthesis sites of the peptides shown in (A) correspond to the visible grey ovals or rectangles in (B). The paper strips are blocked with milk powder in PBS and incubated with anti-FLAG M1 antibody or an anti-actin antibody. The bound first antibody is detected with peroxidase-conjugated goat anti-mouse antibody (substrate 13) or with alkaline phosphatase conjugated goat anti-mouse antibody (substrate 14).

FIG. 21: Linkage of the nucleoside with DMTr protective group at the 5'-OH end to the NH2 groups anchored on a solid substrate FIG. 22: Usual protective groups (for the bases and for the phosphate groups) in oligosynthesis.

Figure 23:
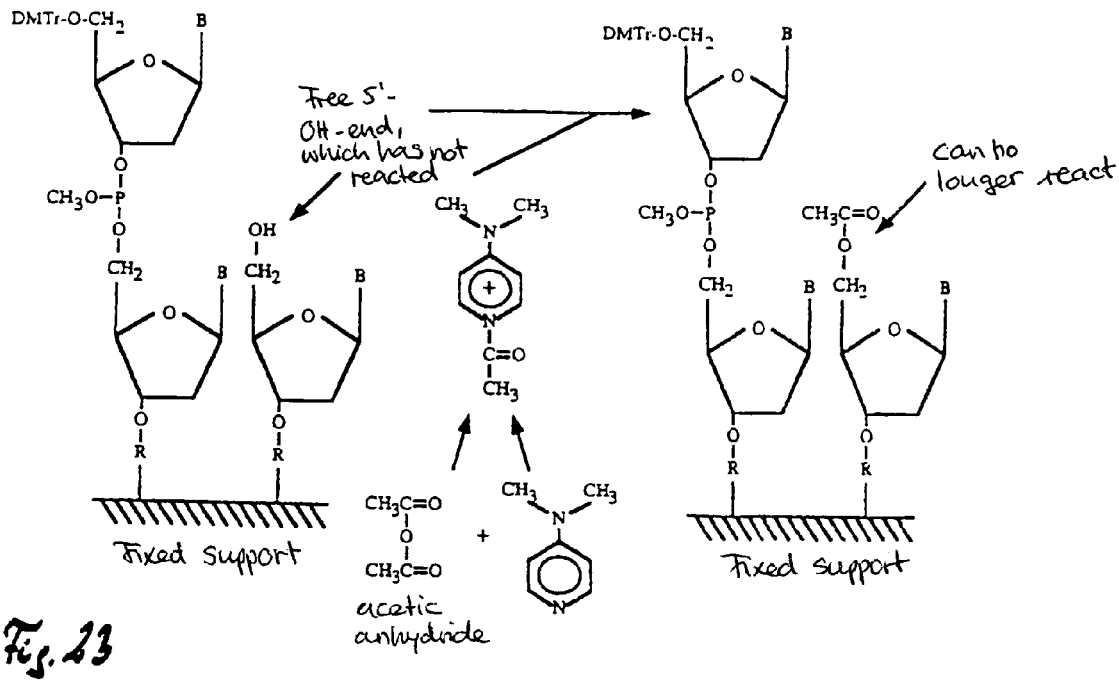

FIG. 23: "Capping" of non-reactive 5'OH ends.

Figure 24:
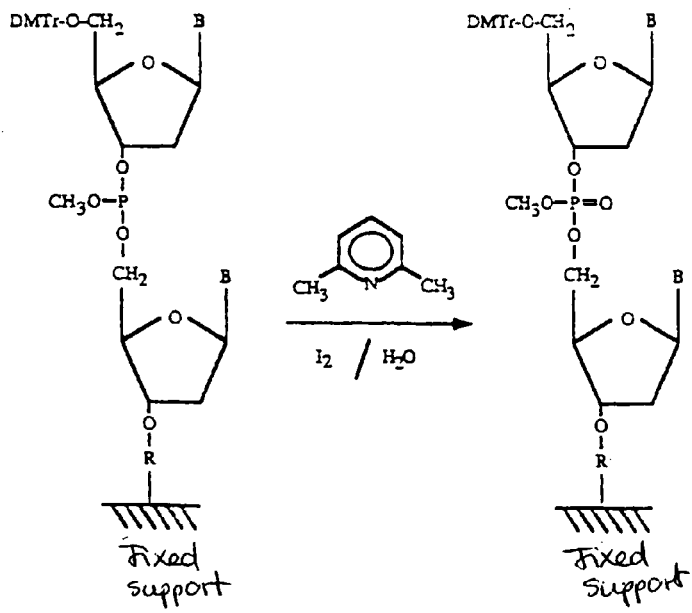

FIG. 24: Oxidation of trivalent phosphate groups.

Figure 25:
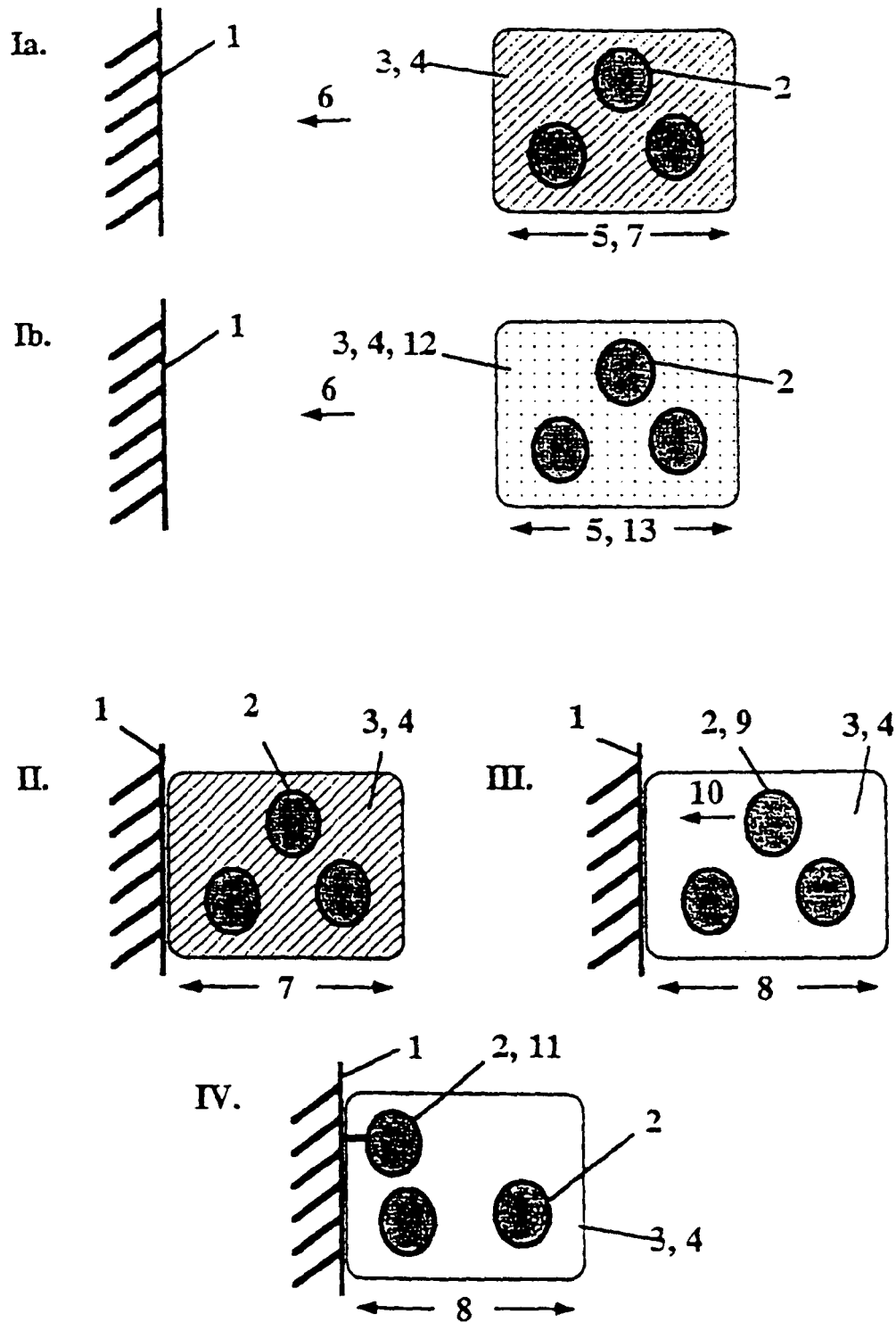

FIG. 25 Schematic illustration of a method wherein substances, such as monomers for the combinatorial synthesis of molecule libraries, are first embedded in a matrix that includes at least one solvent.

a) CONVERSION OF A COLOR LASER PRINTER INTO AN OLIGOMER SYNTHESIS MACHINE (FIG. 13)

The program control of a commercially available color laser printer is modified in this respect such that:
  The support (especially for peptide synthesis or oligonucleotide synthesis derivatised copying film consisting mainly of polystyrene or for peptide synthesis or oligonucleotide synthesis derivatised paper) linked to the support roller (or to the transfer roller) remains fixed on the support roller (or on the transfer roller) until an external control signal terminates this fixing to the support roller,
  instead of four different alternative magnetic rollers with attached toner containers 24 different alternative magnetic rollers with attached toner container control in the vicinity of the writable roller.

Alternatively the transfer unit can also be used one after the other in six modified color laser printers which each contain four different toner containers. Thus, a total of up to 24 different toner particles in one layer is applied to the transfer unit. The different positioning of the laser according to the equipment is measured beforehand and taken into account in the composition pattern.
  In addition, an external device is constructed including
  A heater unit, especially using infrared light or a hot air blower
  A rotating roller with which various fluids can be transferred to the support fixed on the support roller or the transfer unit in a time-programmable fashion
  A rotating roller with which various fluids can be lead off from the support fixed to the support roller in a time-programmable fashion.

b) CONVERSION OF ANOTHER COLOR LASER PRINTER TO AN OLIGOMER SYNTHESIS MACHINE (FIG. 14)

A support is fixed to the endless belt of a transfer roller of a commercially available color laser printer. On the support, but especially on the transfer unit there are applied structures recognisable by an optoelectronic scanner unit which allow the position of the transfer unit and thus the position of the support fixed thereon to be adjusted relative to the position of the laser responsible for transferring the toner particles in a feedback mechanism.
  In addition, an external device is constructed including
  A heater unit, especially using infrared light or a hot air blower
  A trough with which various fluids can be transferred to the support fixed on the transfer unit in a time-programmable fashion
  A rotating roller with which various fluids can be lead off from the support fixed to the support roller in a time-programmable fashion.
  Said transfer unit with the support fixed to it can be removed from said other color laser printer between individual linking cycles and inserted in said other external device. After various fluids have been supplied and led off, said transfer unit can be re-adjusted precisely relative to the position of the laser responsible for transferring the toner particles using said optoelectronic scanner unit.

c) MANUFACTURE OF AMINO ACID TONERS

Various amino acids provided with protective groups, especially fMoc protective groups, especially also the corresponding anhydrides together with magnetite particles are dissolved in diphenyl formamide at 75° C., shock-frozen and finely ground, so as to produce particles as uniform as possible, approx. 1-200 µm in diameter, especially 5-40 µm in diameter. These particles are loaded into toner cassettes and printed on paper. FIG. 19 compares the print quality of a normal toner with various amino acid toners.

d) MANUFACTURE OF PHOSPHORAMIDITE TONER PARTICLES

Various phosphoramidites provided with protective groups together with magnetite particles are dissolved in diphenyl formamide/acetonitrile at 25° C., shock-frozen and the soluble constituent sublimed at low temperatures. They are then finely ground so as to produce particles as uniform as possible, approx. 1-200 µm in diameter, especially 2-40 µm in diameter. These particles are loaded into toner cassettes and printed on paper.

e) SYNTHESIS OF A PEPTIDE ARRAY USING A LASER PRINTER

The amino acids described in example (c) (see also FIG. 19) are used to synthesise two peptide patterns intermeshing in a checkerboard pattern. First paper is derivatised by standard methods using free amino groups. Then two other amino acids are linked uniformly to the paper using standard methods. Using the individual amino acid toners described in example (c) a checkerboard pattern of ovals and then, after changing the toner cassette, an intermeshing pattern of rectangles is printed on the derivatised paper. A total of five layers of amino acids is thus printed, each followed by linking of the amino acids provided with protective groups contained in the amino acid toners and detachment of the N-terminal protective group. In another step a last N-terminal amino acid is linked uniformly using standard methods, followed by detachment of the protective groups at the side chains of the peptide chain using standard methods. In this way two checkerboard intermeshing patterns of peptides (N-terminal)-DYKDDDDK-(support) and (N-terminal)-DDEETTDK-(support) are synthesised.

f) DETECTION OF A PEPTIDE PATTERN SYNTHESISED USING A LASER PRINTER USING STANDARD METHODS

The derivatised paper described in example (e) to which two checkerboard intermeshing peptide patterns were linked, is cut into smaller pieces and first non-specific linkages are blocked using a suitable aqueous solution, such as for example 2% milk powder in PBS. Two different monoclonal antibodies (from mouse) are diluted in the same buffer. Then various pieces of paper are stained with one or other of the monoclonal antibodies by shaking gently for 60 minutes, and then washed three times. The goat anti-mouse antibody linked to the enzyme is diluted in 2% milk powder in PBS; the support is then wetted with this by shaking gently for 60 minutes and then washed three times. FIG. 20 shows the subsequent staining of the pieces of paper with various enzyme substrates: the monoclonal mouse antibody FLAG M1 (Sigma) specifically recognises the peptide (N-terminal)-DYKDDDDK-(support) or the checkerboard peptide pattern of rectangles generated using a laser printer.

g) SYNTHESIS OF A COMPLETE 5-MER PEPTIDE LIBRARY USING AN ADAPTED COLOR LASER PRINTER

A suitable flat support is derivatised with free amino acid groups using standard methods. Paper or copier films essentially consisting of polystyrene are especially suitable for this. Using standard fMoc peptide synthesis under anhydrous conditions familiar to the specialist, a suitable spacer, especially 2-3 amino acids long, is first synthesised at the free amino groups of the support. Optionally 2 or 3 other layers of linked amino acids, preferably amino acid mixtures of 19 or 20 different amino acids (i.e. optionally omitting cysteine), can be added to this spacer by standard methods. The derivatised support is then attached to the support roller or the transfer unit of the modified color laser printer described in example (a) or in example (b).

The toner containers of the modified color laser printer described in example (a) or (b) contain various amino acid toners described in example (c).

Then the printing process is started so that especially 19 or 20 different amino acid toners are printed in precise positions next to each other essentially using the operating principle of a normal color laser printer. The support is thereby separated into 19 or 20 separate, precisely defined regions. Linking of the activated amino acids printed in precise positions, especially amino acid anhydrides, then takes place at approximately 65° C. for 5-30 minutes. During this process the support roller (or the transfer roller) with the derivatised support fixed securely to it rotates uniformly under a row of infrared lamps which was described as a heater unit in example (a) or example (b).

Then, the unconverted amino acid toner as described in example (a) or in example (b) is washed away, the fMoc protective group is detached using standard methods, washed again and then the support is dried using a heater unit described in example (a) or in example (b). During this time the support remains securely fixed to the support roller (or the transfer roller) which rotates uniformly throughout the entire time.

The printing process is then started again so that 19 or 20 different amino acid toners are again printed in precise positions next to one another or above one another. This time the support is preferably divided into $19^2$ or $20^2$ precisely defined regions. As just described, the activated amino acids are linked to the support, the unconverted amino acid toner is washed away and the fMoc protective groups detached.

Three more similar printing processes thus divide the support preferably into $19^5$ or $20^5$ precisely defined regions. Optionally two or three more layers of linked amino acids, preferably amino acid mixtures of 19 or 20 different amino acids (i.e., optionally omitting cysteine), can be added to the free amino terminals.

Finally, all protective groups, including those of the side chains are detached with 10% silane in concentrated trifluoroacetic acid, the support is washed and dried with DMF and methanol so that a support with, for example, $20^5=3,200,000$ different regions is produced in the final effect, which each represent one of all possible naturally occurring C-terminal linked pentapeptides.

h) SYNTHESIS OF A COMPLETE 12-MER OLIGONUCLEOTIDE LIBRARY ON A SUPPORT USING A MODIFIED COLOR LASER PRINTER

As described in example (d), four different phosphoramidite toner particles are produced, which preferably contain four different activated monomers for the oligonucleotide synthesis. These toners are loaded into toner containers and printed on a carrier as described in example (a) or (b) using a modified color laser printer.

As described in example (h) for the synthesis of a complete 5-mer peptide library, a suitable support with free amino groups (or hydroxyl groups) manufactured by standard methods is used. If not already present as a result of the first step, a suitable linker is synthesised at the free amino groups (or hydroxyl groups) using standard synthesis under anhydrous conditions familiar to the specialist, which again anchors free amino groups (or hydroxyl groups) on the support, which this time however are approximately 22 atoms away from the surface.

As described in example (g) for the synthesis of a complete 5-mer peptide library, the monomers located in the four different phosphoramidite toner particles are mobilised by the heater unit after they had been activated with tetrazole. Then they link to the support for 2-10 minutes.

Linking of the activated phosphoramidite (with protective groups) to the solid support, detachment of the protective groups and the washing steps take place under standard conditions for oligonucleotide synthesis familiar to the specialist.

As described in example (g), the unconverted phosphoramidite toner is washed away as described in example (a) or (b), the DMTr protective group is detached from the 5'-end of the phosphoramidite using standard methods, washed again and then the support is dried using the heater unit described in example (a) or (b). During this time the support remains fixed securely on the support roller.

Examples for the protective groups used are:
4',4'-dimethoxytrityl chloride (DMTr) for the 5'-end of the phosphoramidite (FIG. 21)
Benzoyl for the bases adenine and cytosine (FIG. 22)
Isobutyryl for the base guanine (FIG. 22)
Methoxy or beta-cyanoethyl for the phosphate groups (FIG. 22)

After the monomers have been linked to the support, any free 5'-OH ends remaining at every step are provided with a "cap" so that they cannot participate in later reactions (FIG. 23). A last step in which trivalent phosphate groups are oxidised concludes the synthesis cycle (FIG. 24).

After detachment of the DMTr protective group from the 5'-end of the phosphoramidite, the support is printed again in the next step as described in example (g) so that the support is this time divided into preferably $4^2$ separate regions. In each of these separate regions there is situated one of 16 possible dinucleotides linked to the support via the 3'-end through a spacer, whose 5'-end carries a free OH group.

This process is repeated a total of 10× with, for example, all four activated phosphoramidites in each case so that the 16 separate regions described above are then divided into a total of $4^{12}$ precisely defined regions, at each synthesis step followed by "capping" of remaining free 5'-OH ends as described above, oxidation of the trivalent phosphate groups and renewed detachment of the DMTr protective groups with TCA.

The synthesis described above is consistent with the standard oligonucleotide synthesis familiar to the specialist. Unlike the familiar standard synthesis, the oligonucleotides are anchored on the solid support such that after the final complete detachment of the protective groups they cannot be detached from the support but remain linked to the support.

Finally, all protective groups are detached using dichloromethane and trichloroacetic acid, the support is washed with acetonitrile and dried so that in the end effect a support with $4^{12}=16,777,216$ different regions is produced, each representing one of all possible 12 mer oligonucleotides linked via the 3'-end.

i) SYNTHESIS OF A PEPTIDE ARRAY USING AN INK JET PRINTER

Various different amino acids provided with protective groups, especially with fMoc protective groups, especially also the corresponding anhydrides are dissolved together with isopropanol or NMP and diphenyl formamide. These liquids are poured into multicolor toner cartridges, placed in an essentially commercially available color ink jet printer and printed on paper as in the method described in example (g).

The ink jet printer described is previously modified by analogy with the color laser printer described in example (a) or (b) so that the support remains fixed relative to the printing head during the repetitive printing cycles whereby preferably one rotating support roller is used. As described in example (a) or (b) an external device is built including
A heater unit, especially using infrared light or a hot air blower
A rotating roller with which various fluids can be transferred to the support fixed on the support roller in a time-programmable fashion
A rotating roller with which various fluids can be lead off from the support fixed to the support roller in a time-programmable fashion.

A suitable flat support is derivatised with free amino groups using standard methods. Paper or copier film essentially consisting of polystyrene is especially suitable for this. Using standard fMoc peptide synthesis under anhydrous conditions familiar to the specialist, a suitable spacer, especially 2-3 amino acids long, is first synthesised at the free amino groups of the support. Optionally 2 or 3 other layers of linked amino acids, preferably amino acid mixtures of 19 or 20 different amino acids (i.e. optionally omitting cysteine), can be added to this spacer by standard methods.

The support can then be optionally soaked with a mixture of dichloromethane and diphenyl formamide. The dichloromethane is vaporised during the transfer whereby the derivatised paper is fixed on a support which can be moved relative to the print unit of the modified color ink jet printer described above.

Then the printing process is started so that especially 19 or 20 different amino acid toners are printed in precise positions next to each other essentially according to the operating principle of a normal color ink jet printer. Linking of the activated amino acids printed in specific positions then takes place at approximately 65° C. for 5-30 minutes. During this process the support roller with the derivatised support fixed securely onto it rotates uniformly under a row of infrared lamps which were described as the heater unit in example (a) or (b).

Then, the unconverted amino acid toner is washed away with the aid of the rollers described above, the fMoc protective group is detached using standard methods and the support is then dried using the heater unit described above. During this time the support remains fixed securely to the support roller which rotates uniformly over the entire time.

The printing process is then started again so that again 19 or 20 different amino acid toners are printed in precise positions next to one another or above one another. By this means the support is this time divided preferably into $19^2$ or $20^2$ precisely defined regions. As just described, the activated amino acids are linked to the support, the unconverted amino acid toner is washed away and the fMoc protective groups detached.

Three other similar printing processes thus divide the support preferably into $19^5$ or $20^5$ specifically defined regions. Optionally 2 or 3 other layers of linked amino acids, preferably amino acid mixtures of 19 or 20 different amino acids (i.e. optionally omitting cysteine), can be added to the free amino terminals of this peptide array using standard methods.

Finally, all protective groups, including those of the side chains are detached with 10% silane in concentrated trifluoroacetic acid, the support is washed and dried with DMF and methanol so that a support with, for example, $20^5=3,200,000$ different regions is produced in the final effect, which each represent one of all possible naturally occurring C-terminal linked pentapeptides.

j) EXAMINATION OF BLOOD SERUM USING A SUPPORT WITH PEPTIDE LIBRARY FIXED TO IT

The complete peptide library described in example (g) is stained with the blood serum of a patient for which unspecific linkages are first blocked with a suitable aqueous solution, such as for example, 2% milk powder in PBS and the blood serum is diluted in the same buffer. Then the support is wetted with the serum by gently shaking for 60 minutes and then washed three times.

Bound human antibodies from the blood serum are detected using standard methods. Goat anti-human antibody or antibody binding proteins such as protein G or protein A are used for this purpose. These detection reagents are linked to enzymes such as peroxidase or phosphatase or to dyes or radioactive substances such as Cy5 or iodine 131.

The detection reagents are diluted in 2% milk powder in PBS, the support is wetted with this by gently shaking for 60 minutes and then washed three times. The activity of the enzymes produces a colored precipitate which can be read out using commercially available scanners. Locally precise detection of the bound radioactivity or fluorescence is accomplished using commercially available phosphoimagers.

The signals are divided into a total of 10 different signal stages which are each assigned to different pentapeptides of the peptide array.

k) IDENTIFICATION OF DISEASE-SPECIFIC REACTIVITIES IN BLOOD SERUM USING A SUPPORT WITH PEPTIDE LIBRARY FIXED TO IT

The pentapeptide libraries described in example (g) are stained using blood serum from 50 patients with gastric ulcers as described in example (j). Here several patient serums can be mixed together or an array can be stained for each serum. Then the average of the signal strength from several stainings is determined for each peptide in the array.

The same procedure is followed using 50 control serums. Here also the average of the signal strength from several stainings is determined for each peptide.

By comparing the averages it is possible to identify several peptides which are stained significantly more intensely by the patient serums than by the corresponding control sera. This result is shown schematically in FIG. 16. A data base search using these peptide sequences yields a relationship between these peptides and the gene products of the bacterium Helicobacter pylori.

l) EXAMINATION OF PATIENT DNA USING A 12-MER OLIGONUCLEOTIDE LIBRARY FIXED TO A SUPPORT

The support described under example (h) with a complete oligonucleotide library fixed to it is stained with patient DNA. Standard methods familiar to the specialist are used. Non-specific linkages are saturated using, for example, DNA from herring spermatozoa.

A tumour tissue sample and a healthy tissue sample were taken simultaneously from the patient and the genomic DNA contained therein is multiplied with the aid of one or several pairs of tumourgen-specific primers (specific for example for the genes of p53, p16, ras, c-myc, n-myc) in a polymerase chain reaction. The tumour sample is marked for example with fluoroscein-12-dUTP whereas the normal sample is marked for example with tetramethyl-rhodamine-5-dUTP. The samples are mixed together and hybridised on the support.

Locally specific detection of the bound fluorescences (or radioactivity) is accomplished using commercially available phosphoimagers as described in example (j). Here the ratio of green to red fluorescence or the resultant mixed color is determined for example. The signals are each assigned to the various 12-mer oligonucleotides of the array.

In this way point mutations in genes which are important for the prognosis of tumour diseases can be diagnosed. In contrast to the systems available on the market, many genes can be analysed at the same time with a complete 12-mer oligonucleotide library.

In an alternative method, DNA taken from the patient is used as a template for the multiplication of so-called Alu primers which hybridise at the edges of repetitive Alu sequences occurring very frequently in the genome and multiply the non-repetitive DNA lying between two Alu sequences. Again the tumour sample is marked, for example, with fluorescein-12-UPT whereas tetramethyl-rhodamine-5-dUTP is incorporated into the normal sample. The samples are mixed together as described above and then hybridised on the support.

The fluorescence signals are then read out as described above. In this way a very large part of the genome is scanned for differences between normal and tumour tissue as a result of which new diagnostic markers may be discovered which yield important information for the tumour progression.

While the invention has been illustrated and described as embodied in a method and devices for applying substances to a support, especially monomers for the combinatorial synthesis of molecule libraries it is not intended to be limited to the details shown since various modifications and structural changes may be made without departing in any way from the spirit of the present invention.

LIST OF REFERENCE CHARACTERS

1 Support
2 Substances
3 Matrix
4 First solvent
5 Transport unit
6 Movement in direction of support (1)
7 Solid or gel-like state of aggregation
8 Modified physical environment
9 Mobilised substances
10 Movement in direction of support surface (1)
11 Substances (2) covalently linked to support (1)
12 Second solvent
13 Liquid state of aggregation
14 Protective group
15 Protective group detachable by light
16 Electromagnetic waves, light
17 Light-sensitive protective layer
18 Precisely defined region on an array or support (1)
19 Toner particles, transport unit
15 Toner reservoir
21 Magnetic roller
22 Roller writable with laser light 23 Charged toner particles jump onto writable roller (22)
24 Toner particles on carrier (1)
25 Hot roller
26 Molten or mobilised toner particle
27 First colour printed on paper
28 Second colour printed on paper
29 Third colour printed on paper
30 Fourth colour printed on paper
31 Toner reservoir containing toner particles (19) of first colour
32 Toner reservoir containing toner particles (19) of second colour
33 Toner reservoir containing toner particles (19) of third colour
34 Toner reservoir containing toner particles (19) of fourth colour
35 Support roller or transfer unit of a colour laser printer
36 Supply of linking reagents, washing solutions or gaseous substances
37 Scanner unit
38 A pattern applied to the support (1)
39 Comparison of pattern measured with scanner unit with the same previously stored pattern
40 Electronic displacement of image in printer memory by the deviation from the desired value
41 Unused
42 Peptides recognised by patient serums and by control sera
43 Peptides specifically recognised by patient sera
44 D-peptides of the array which bind the enzyme
45 D-peptides of the array which bind and at the same time inactivate the enzyme
46 Magnetic component
47 Meltable plastic component
48 Chromophores
49 Monomer for the combinatorial synthesis substance (2)
50 Solvent in solid state of aggregation

What is claimed is:

1. A method for applying substances including monomers to a support for the combinatorial synthesis of molecule libraries, comprising the steps of:

embedding at least one amino acid monomer or nucleotide monomer into a matrix of at least one solvent that at a temperature of less than 90° C. is in a solid state of aggregation, thereby forming monomer-immobilizing transport units;

applying these transport units in the solid state of aggregation onto a solid support by laser printing at a temperature of less than 90° C., whereby the transport units become electrostatically charged and thereby transferred onto pre-determined regions of a laser-writable roller and thereafter applied to the support, where the transport units are remaining in the solid state of aggregation;

thereafter, changing the transport units from a solid state of aggregation to a liquid state of aggregation thereby mobilizing the monomers and diffusing the monomers within the transport units, and thereafter, covalently linking the thus mobilized monomers to molecules located on the support through a linking reaction, thereby yielding a number of different monomers coupled to the support in the pre-determined locations and washing away non-linked monomers applying in this manner more than one layer of monomers to the support, whereby monomers from a second layer are covalently linked to monomers from a first layer that were previously linked to the support and washing away the non-linked monomers.

2. The method of claim 1, wherein the temperature at the embedding step is in a range between −10° C. and 80° C.

3. The method of claim 2, wherein the range is between 0° C. and 40° C.

4. The method of claim 1, wherein the laser printing is carried out with one selected from the group consisting of laser printer, laser copier and arrays of micro lasers.

5. The method of claim 1, wherein mixtures of amino acid monomers or oligonucleotide monomers are used.

6. A method for applying substances to a support for the combinatorial synthesis of molecule libraries, comprising the steps of:
embedding amino acid or nucleotide monomers into a matrix that includes at least one solvent at a temperature of less than 90° C. at a solid state of aggregation thereby forming toner particles that serve as transport units, said toner particles differ from each other by the monomers immobilized within;
electrostatically charging said toner particles and positioning by laser printing, at different times, the toner particles in predetermined position to a solid support, whereby the toner particles remain in a solid state of aggregation and the monomers within the toner particles are temporarily blocked from coupling to the support;
changing the toner particles from a solid state of aggregation to a liquid state of aggregation, thereby mobilizing the monomers and diffusing the monomers within the toner particles and thus permitting release of the monomers onto the support;
covalently linking the thus released monomers to molecules located on the support through a linking reaction, thereby yielding a number of different monomers coupled to the support,
wherein more than one layer of monomers is applied repeatedly one after the other to the support in defined positions, in each case followed by the covalent linking of the substances to the support and washing away non-linked substances.

7. The method of claim 1, wherein the mobilizing step is carried out by one of the elements selected from the group of applying electromagnetic waves, applying electrical voltage and applying thermal energy.

8. The method of claim 7, wherein the electromagnetic waves are laser light.

9. The method of claim 1, wherein the transport units have a particle size in a range between 0.2 μm and 200 μm at a solid state of aggregation at a temperature of less than 90° C.

10. The method of claim 9, wherein the temperature is less than 50° C.

11. The method of claim 9, wherein the particle size is between 2 μm and 40 μm.

12. The method of claim 1, wherein the support is held at a temperature of at least 10° C. lower as compared to the temperature of the transport units until starting the linking reaction of the monomers to the molecules on the support.

13. The method of claim 1, wherein the monomers on the support are cooled and frozen.

14. The method of claim 1, wherein the monomers include at least one element or bind to such particles that include an element selected from the group consisting of: diphenyl formamide; monomers, dimmers, trimmers suitable for combinatorial synthesis; D amino acids, L amino acids, nucleosides, derivatized nucleosides or mirror images, or derivatives thereof; polystyrene and cellulose.

15. The method of claim 1, further comprising the step of, after the linking reaction, detaching protective groups by standard methods so as to form free amino- or hydroxyl groups for linkage with monomers.

16. The method of claim 1, wherein the support used is one or more selected form the group consisting of polystyrene films, paper, CDs, MODs, DVDs or FMDs.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial sequence
<220> FEATURE:
<223> OTHER INFORMATION: checkerboard intermeshing patterns of peptides
      that are synthesised.
<220> FEATURE:
<221> NAME/KEY: PEPTIDE
<222> LOCATION: (1)..(8)

<400> SEQUENCE: 1

Asp Tyr Lys Asp Asp Asp Asp Lys
1               5

<210> SEQ ID NO 2
<211> LENGTH: 8
<212> TYPE: PRT
<213> ORGANISM: Artificial sequence
<220> FEATURE:
<223> OTHER INFORMATION: checkerboard intermeshing patterns of peptides
      that are synthesised.
<220> FEATURE:
<221> NAME/KEY: PEPTIDE
<222> LOCATION: (1)..(8)

<400> SEQUENCE: 2

Asp Asp Glu Glu Thr Thr Asp Lys
1               5
```